(12) United States Patent
Konno et al.

(10) Patent No.: US 8,006,561 B2
(45) Date of Patent: Aug. 30, 2011

(54) DETECTION SENSOR

(75) Inventors: Mitsuo Konno, Tsukuba (JP); Tsuyoshi Ikehara, Tsukuba (JP); Takashi Mihara, Tokyo (JP)

(73) Assignees: National Institute of Advanced Industrial Science and Technology, Tokyo (JP); Olympus Corporation, Tokyo (JP)

( * ) Notice: Subject to any disclaimer, the term of this patent is extended or adjusted under 35 U.S.C. 154(b) by 359 days.

(21) Appl. No.: 12/293,348

(22) PCT Filed: Jun. 1, 2007

(86) PCT No.: PCT/JP2007/061170
§ 371 (c)(1),
(2), (4) Date: Nov. 25, 2008

(87) PCT Pub. No.: WO2007/148522
PCT Pub. Date: Dec. 27, 2007

(65) Prior Publication Data
US 2009/0199639 A1 Aug. 13, 2009

(30) Foreign Application Priority Data

Jun. 22, 2006 (JP) ................................. 2006-172217
Feb. 26, 2007 (JP) ................................. 2007-046199

(51) Int. Cl.
*G01N 29/036* (2006.01)
*G01N 29/02* (2006.01)
(52) U.S. Cl. .............. 73/649; 73/24.06; 73/579; 73/662
(58) Field of Classification Search ................... 73/649, 73/24.06, 579, 652, 662
See application file for complete search history.

(56) References Cited

U.S. PATENT DOCUMENTS

| 4,333,029 | A   | * | 6/1982  | Kolm et al. ................... 310/329 |
| 7,159,463 | B2  | * | 1/2007  | Dayagi et al. ................... 73/579 |
| 7,681,433 | B2  | * | 3/2010  | Konno et al. ................ 73/24.06 |
| 7,795,008 | B2  | * | 9/2010  | Dayagi et al. ............. 435/287.2 |
| 2005/0225413 | A1 | * | 10/2005 | Kozicki et al. .................. 335/78 |

FOREIGN PATENT DOCUMENTS

| JP | 63-144233   | 6/1988  |
| JP | 2001-56278  | 2/2001  |
| JP | 2006-329931 | 12/2005 |
| JP | 2007-187485 | 7/2007  |
| WO | 99-13300    | 3/1999  |

OTHER PUBLICATIONS

International Search Report for PCT/JP2007-061170; completed Aug. 24, 2007.

* cited by examiner

*Primary Examiner* — J M Saint Surin
(74) *Attorney, Agent, or Firm* — Pearne & Gordon LLP

(57) ABSTRACT

It is an object of the present invention to provide a technique that can realize improvement of sensitivity of a vibrator. A platform 50 to which a substance adheres or sticks is provided to be mechanically coupled to a vibrator 20 of a sensor via bridges 51. Sensitivity of the sensor is improved by causing the mass of a substance adhering or sticking onto the platform 50 as if the substance concentratedly adheres or sticks to places where the platform 50 is connected to the vibrator 20. It is preferable to connect, via the bridges 51, the platform 50 to places where the platform 50 vibrates integrally with the vibrator 20. For this purpose, it is preferable to mechanically couple, via the bridges 51, the platform 50 to regions where vibration occurs only in one of an r direction or a θ direction in the vibrator 20.

15 Claims, 19 Drawing Sheets

U(Rb) ————
U(Ra) ------------
V(Rb) —·—·—
V(Ra) ━━━━

U(Rb) ———
U(Ra) ---------
V(Rb) —·—·—
V(Ra) ━━━

U(Rb) ————
U(Ra) --------
V(Rb) —·—·—
V(Ra) ━━━

DETECTION SENSOR

TECHNICAL FIELD

The present invention relates to a detection sensor suitable for use for performing detection of presence or absence of a substance having mass, detection of the mass of a substance, and the like, and, more particularly to a detection sensor including a micro-mechanical vibrator employing an MEMS (Micro Electro Mechanical Systems) technology.

BACKGROUND ART

According to the progress of micro-processing technologies such as a macro-machine/MEMS technology, it is possible to manufacture mechanical vibrators in extremely small sizes. This makes it possible to create the mass of the vibrators themselves very small. Consequently, a vibrator that is so highly sensitive that fluctuation in frequency and impedance characteristics is caused by even a change in mass due to adhesion of very fine substances (e.g., molecules and viruses) on a molecule level is being realized. If the highly sensitive vibrator is used, it is possible to configure a sensor and the like that can detect presence of a very fine substance and an amount of the substance.

A device that detects an amount of a substance according to, for example, a frequency change in a mechanical vibrator is well-known as a QCM (Quarts Crystal Micro balance) sensor. This is a sensor that makes use of a characteristic that, when a substance adheres to a quarts vibrator, a vibrator frequency fluctuates (falls) according to the mass of the adhering substance. The QCM sensor has excellent performance as a mass sensor that measures very small mass. A system for detecting an amount of a substance according to, for example, a frequency change in a mechanical vibrator is also often used as a thickness meter (a vapor deposition monitor).

In such a vibrator, in particular, a micro-mechanical vibrator employing the MEMS technology, since a size thereof has been substantially reduced, a frequency of the vibrator has increased to a GHz level. Moreover, since the micro-mechanical vibrator employing the MEMS technology can be made of an Si material, the technology is being developed into a research aiming at integration with a semiconductor circuit.

As high-frequency filters actively used in personal radio communication devices and the like such as cellular phones, there are a dielectric resonator that mainly realizes a reduction in size and improvement of performance of an electric resonator, a surface wave filter (SAW Filter) that makes use of a characteristic of a sound wave, a quartz crystal filter that uses a mechanical vibration characteristic of a crystal vibrator, and the like. The high-frequency filters are widely used in high-frequency units and the like of cellular phones by making use of characteristics thereof, respectively. However, there is also a strong demand for a reduction in price as well as a further reduction in size and improvement of performance such as an increase in frequency of radio devices. Therefore, in place of these conventional filters, a high-frequency filter of a new system that can be reduced in size and price through integration with a semiconductor integrated circuit (i.e., formation as one-chip) is demanded. Since Si same as a material of a semiconductor is used as a material of a mechanical vibrator manufactured by an MEMS processing technology, the mechanical vibrator is a prospective candidate of the high-frequency filter. Therefore, basic researches for the purpose of an increase in frequency of an MEMS vibrator, an increase in Q value (high quality factor), and the like and applied researches for application to high-frequency filters, transmitters, and the like employing the MEMS vibrator are also actively performed (see, for example, Non-Patent Document 1).

As one type of such vibrators, there is a disc-like vibrator. Basic researches concerning mechanical vibrator of the disc-like vibrator have been performed since long time ago. It may be said that basic researches of vibration modes and the like for defining vibration states of the disc-like vibrator have already been finished.

Non-Patent Document 1: C.T.-C. Nguyen, "Vibrating RF MEMS Technology: Fuel for an Integrated Microchemical Circuit Revolution?." The 13th International Conference on Solid-State Sensors, Actuators and Microsystems (Transducers '05), Korea, Jun. 5 to 9, 2005

DISCLOSURE OF THE INVENTION

However, in the sensors and the filters employing the vibrators, vibration characteristics of which are changed by adhesion of very small mass, a further improvement of sensitivity, a further reduction in size, and a further reduction in price are always demanded. Therefore, as research subjects involved in the adaptation of the MEMS in the disc-like vibrator, for example, there is characteristic control by combinations of vibrators for the purpose of improvement of a Q value for improvement of sensitivity and application to an vibrator driving and detection method and a filter. Concerning these research objects, researches have been continuously performed concentratedly.

It is an object of the present invention to provide a technique that can realize further improvement in sensitivity of a vibrator among the technical subjects described above.

The detection sensor in the present invention includes a disc-like vibrator, a driving unit that vibrates the vibrator, and a detection unit that detects a change in the vibration in the vibrator to thereby detect a substance. Such a detection sensor detects a change in vibration of the vibrator caused by the influence of the mass of a substance to thereby detect the substance. As the detection of a substance, not only detection of presence or absence of the substance but also detection of an amount of the substance is possible.

Such a vibrator vibrates in a specific resonance mode. Therefore, an area in which amplitude is large and an area that hardly vibrates are formed on the surface of the vibrator. Moreover, the areas are different depending on a resonance mode. Consequently, there is a problem in that detection sensitivity is different depending on where on the surface of the vibrator a substance that should be detected adheres to. The inventors who paid attention to this problem reached an idea that, since sensitivity fluctuated depending on a region even if the substance uniformly adhered or stuck to the surface of the vibrator, there was a room of improvement of sensitivity in this sense.

Means for realizing improvement of sensitivity in a vibrator is means for concentratedly and selectively causing a substance to adhere or stick to a region where sensitivity is high (amplitude is large). The applicant has already proposed this means (Japanese Patent Application No. 2006-4197).

The applicant has also already proposed a method of, making use of a characteristic that amplitude of a vibrator is different depending on a region, controlling a loss due to prevention of vibration of the vibrator and realizing improvement of sensitivity by supporting the vibrator in a region where vibration is small (Japanese Patent Application No. 2006-73742).

The invention devised by the inventors this time has a main point in providing a platform, to which a substance is caused to adhere or stick, in a vibrator by mechanically coupling the platform thereto.

In other words, a detection sensor of the present invention is characterized by including a disc-like vibrator, a platform that is mechanically coupled to the vibrator and to which a substance having mass adheres or sticks, a driving unit that causes the vibrator to vibrate, and a detection unit that detects a change in vibration in the vibrator to thereby detect the substance.

Consequently, the influence of the mass of the substance adhering or sticking onto the platform is transmitted from a coupling portion to the vibrator. Therefore, the mass of the substance adhering or sticking onto the platform behaves as if the substance adheres or sticks onto a portion where the platform is coupled in the vibrator (this may be hereinafter referred to as coupling portion). In this case, if the platform is provided not to resonate with the vibrator but to behave integrally with the vibrator, the platform behaves with a vibration characteristic of the vibrator in the coupling portion. Consequently, the vibration of the vibrator changes as if the substance adhering or sticking to the entire platform (concentratedly) adheres or sticks to the coupling portion of the vibrator. On the platform, since the same sensitivity is shown in any region, an area of a portion to which the substance adheres or sticks substantially increases. Consequently, improvement of sensitivity of the vibrator as a whole can be realized.

By setting a resonance frequency of the platform higher than that of the vibrator, the platform is not excited by the vibrator and the platform is not affected by the influence of the vibration of the vibrator.

To cause the platform and the vibrator to integrally behave, it is preferable to couple the platform to the vibrator in a region where vibration occurs in only one of a Radial direction (a radial direction of the vibrator) or a Tangential direction (a rotating direction around the center of the vibrator) of the vibrator in the vibrator. In this case, the platform is coupled to the vibrator in one or more places. However, it is preferable to couple the platform in two or more places in positions point-symmetrical or line-symmetrical with respect to the center of the vibrator. Consequently, depending on a vibration mode of the vibrator or connection places by bridges, the platform performs linear vibration in the Radial direction of the vibrator or rotational vibration in the Tangential direction of the vibrator integrally with the vibrator.

It is preferable to couple the platform to a region where amplitude is the largest or a portion near the region in the vibrator. Consequently, it is possible to more highly sensitively detect the influence of the mass of the substance on the platform transmitted from the platform to the vibrator.

If the platform is excited by the vibration of the vibrator, it is likely that this excitation affects the vibrator side and detection sensitivity falls. Therefore, to prevent the excitation of the platform by the vibrator, the platform is preferably formed such that a resonance frequency thereof is higher than a resonance frequency of the vibrator.

The vibrator may be formed in any shape as long as the vibrator is formed in a disc shape. However, an opening may be formed in the center of the vibrator. In that case, the platform may be arranged on an inner side of the opening and coupled to an inner edge of the opening of the vibrator via the bridges.

It is preferable to support such a vibrator in a region where vibration is small to thereby control a loss due to prevention of the vibration of the vibrator and realize improvement of sensitivity.

A Q value as a parameter for evaluating the vibrator depends on whether the vibrator can keep vibration energy. The Q value can be represented as a relation of the following formula:

[Formula 1]

$$\frac{1}{Q_{total}} = \frac{1}{Q_{air}} + \frac{1}{Q_{TED}} + \frac{1}{Q_{anchorLoss}} + \frac{1}{Q_{others}} \quad (1)$$

As main causes of a loss of vibration energy of the vibrator, the following causes are conceivable:

1) a loss $Q_{air}$ due to media around the vibrator such as air;
2) a loss $Q_{TED}$ caused by vibration and deformation of the vibrator;
3) a loss $Q_{anchor\,Loss}$ due to a holding mechanism for the vibrator; and
other losses $Q_{others}$.

To reduce an energy loss due to the media around the vibrator represented by air that determines $Q_{air}$ in 1), the reduction in the energy loss is coped with by controlling the vibration of the vibrator and selecting a vibration mode in which vibration energy of the vibrator is large but energy movement to the media around the vibrator is small. For example, a disc-like mechanical vibrator vibrates only in an inner direction of a disc surface of the vibrator (in terms of a cylindrical coordinate, the vibrator vibrates only in r and θ directions and does not vibrate in a Z direction) and, unlike a film of a drum, rarely vibrates in a direction orthogonal to the disc surface and propagates large vibration energy to the media around the vibrator.

As $Q_{TED}$ in 2), the vibrator vibrates to deform and adiabatic expansion and adiabatic compression are caused by this deformation. Therefore, it is said that an adiabatic expansion area is cooled and, conversely, an adiabatic compression area is heated, temperature inclination occurs in the vibrator, and the temperatures are conducted and averaged, whereby energy is lost. In other words, this energy loss depends on a vibration mode of the vibrator and a material of the vibrator.

$Q_{anchor\,loss}$ in 3) is a loss due to a holding unit of the vibrator and caused by transmission of the vibration of the vibrator to the holding unit. Therefore, it is conceivable that the energy loss can be eliminated by, for example, providing the holding unit in a place where the vibrator does not vibrate. However, in a usual disc-like vibrator of a disc shape, as long as an Si single crystal, which is a most general vibrator material, is used, such a condition has not been found yet.

For example, as a most well-known mode among resonance modes of the disc-like vibrator, there is a Wine-Glass mode (2, 1). Displacement U(r, θ) in the Radial direction and displacement V(r, θ) in the Tangential direction, which are mode functions for the vibrations of such the disc-like vibrator, can be indicated by the following formula:

[Formula 2]

$$U(r, \theta) = \left[A\frac{\partial}{\partial r}J_n(hr) + B\frac{n}{r}J_n(kr)\right]\cos n\theta \quad (2)$$

$$V(r, \theta) = -\left[A\frac{n}{r}J_n(hr) + B\frac{\partial}{\partial r}J_n(kr)\right]\sin n\theta$$

In this formula 2, the Wine-Glass mode (2, 1) means a resonance mode of a minimum frequency at n=2. In this (2, 1) mode, in the Radial direction, r components have finite values in all r's except r=0 of the vibrator and the values change in a circumferential direction according to cos 2θ. Therefore, in the (2, 1) mode, the vibration in the Radial direction is eliminated at angles of θ=π/4, 3π/4, −3π/4, and −π/4. Such a position is referred to as nodal point. A method of holding an vibrator in the position is also proposed.

However, this (2, 1) mode is a Compound mode and has a vibration component in the Tangential direction as well. Therefore, the r components also have finite values for all r's except r=0 in the vibration in the Tangential direction and the values change in the circumferential direction according to sin 2θ. Therefore, at the respective angles of θ=π/4, 3π/4, −3π/4, and −π/4 where U(r, θ) is 0, i.e., cos 2θ is 0, sin 2θ in V(r, θ) is 1, −1, 1, and −1 and, conversely, amplitude is the largest. In other words, in a circular vibrator that vibrates in the Wine-Glass mode (2, 1), a region where both vibrations of a Radial component and a Tangential component are 0 is not present.

However, as a result of concentratedly repeating examinations, the inventors have found a method that allows a region where both vibrations of a Radial component and a Tangential component are 0 on a vibrator to be present unlike the example described above.

In the method found in this way, a vibrator is formed in a ring shape in which an opening is formed in the center. An outer diameter of the vibrator is represented as Ra and an inner diameter thereof is represented as Rb. As displacement in a position r in a position coordinate (r, θ) at the time when this vibrator vibrates, as indicated by formula (3), displacement in the Radial direction is represented as U(r) and displacement in the Tangential direction is represented as V(r). Therefore, the vibrator is formed with the outer diameter Ra and the inner diameter Rb that substantially satisfy U(r)=0 or V(r)=0 when r is Ra or Rb.

[Formula 3]

$$U(r) = \frac{\partial}{\partial r} J_n(hr) + A_6 \frac{n}{r} J_n(kr) + A_7 \frac{\partial}{\partial r} Y_n(hr) + A_8 \frac{n}{r} Y_n(kr) \quad (3)$$

$$V(r) = \frac{n}{r} J_n(hr) + A_6 \frac{\partial}{\partial r} J_n(kr) + A_7 \frac{n}{r} Y_n(hr) + A_8 \frac{\partial}{\partial r} Y_n(kr)$$

Where $$h = \omega \sqrt{\frac{\rho(1-\sigma^2)}{E}},$$

$$k = \omega \sqrt{\frac{\rho(2+2\sigma)}{E}},$$

$$k = h \sqrt{\frac{2}{1-\sigma}}$$

σ: Poisson's ratio of an oscillator material, E: Young's modulus of the oscillator material, ρ: the density of the oscillator material, ω: angular frequency, $A_6$, $A_7$, $A_8$ are coefficients, n is an order of an oscillation mode In formula (3), $A_6$, $A_7$, and $A_8$ are constants uniquely determined according to a peculiar vibration mode defined by the outer diameter Ra and the inner diameter Rb of the vibrator, the Young's modulus, the density, and the Poisson's ratio of the vibrator material, and a boundary condition (in this case, a Free-Free condition) of the vibrator. Specifically, when $A_5$ is set to 1 in formula (9) described later, $A_6$, $A_7$, and $A_8$ are the solutions to a simultaneous linear equation of formula (9).

In this way, in a ring-like vibrator, a region where vibration does not occur in an outer diameter portion or an inner diameter portion may appear depending on a ratio of the outer diameter Ra and the inner diameter Rb of the vibrator. The ratio in this case is different depending on a Poisson's ratio of a material forming the vibrator, a modal number n of a vibration mode in causing the vibrator to vibrate, and an order m of harmonic vibration.

When U(r)=0 or V(r)=0 is substantially satisfied at r=Ra in formula (3), a region where vibration does not occur is present in an outer diameter portion of the vibrator. When U(r)=0 or V(r)=0 is substantially satisfied at r=Rb in formula (3), a region where vibration does not occur is present in an inner diameter portion of the vibrator.

Moreover, when U(r)=0 is substantially satisfied at r=Ra or Rb in formula (3), a region where vibration does not occur is present in a position θ where sin(nθ) is 0 of the vibrator. When V(r)=0 is substantially satisfied at r=Ra or Rb in formula (3), a region where vibration does not occur is present in a position θ where cos(nθ) is 0 of the vibrator.

In this way, it is possible to eliminate both vibrations of the Radial component and the Tangential component in the vibrator.

In the present invention, not only a case in which the condition of U(r)=0 or V(r)=0 is completely satisfied but also a case in which the condition is substantially satisfied is allowed. This is because, due to a manufacturing error and the like, it is difficult to form an vibrator with the outer diameter Ra and the inner diameter Rb that completely satisfy the condition of U(r)=0 and V(r)=0. This is also because, even when the outer diameter Ra and the inner diameter Rb slightly deviate from the condition of U(r)=0 or V(r)=0, vibration may be sufficiently small in the outer diameter portion or the inner diameter portion.

In a region where the condition is satisfied, both the vibrations of the Radial component and the Tangential component can be eliminated. Therefore, it is preferable to hold the vibrator in such a region.

When an opening is formed in the center of the vibrator and the platform is coupled to an inner edge of the opening of the vibrator via the bridges, it is particularly preferable in terms of improvement of sensitivity to drive the vibrator in a (3, 1) mode in which the order m of harmonic vibration is set to 1 and the modal number n of a vibration mode is set to 3.

In this case, when an outer diameter of the vibrator is represented as Ra and an inner diameter of the opening is represented as Rb, Rb/Ra can be set to 0.65 to 0.81. Consequently, a large opening can be formed. By providing the platform in this opening, a detection sensor having a large-area platform can be configured.

The vibrator is supported in plural positions where vibration in the Radial direction and the Tangential direction of the vibrator is substantially zero in the outer diameter portion thereof. In the case of the (3, 1) mode, the supporting positions are located at intervals of an angle of 60° or an angle integer times as large as 60° with respect to the center of the vibrator. In particular, when the vibrator is supported in three positions at intervals of 120° in the outer diameter portion, vibration in the (2, 1) mode in which the order m of harmonic vibration is set to 1 and the modal number n of a vibration mode is set to 2 can be suppressed.

On the other hand, the platform is coupled to the opening of the vibrator in positions where the platform behaves integrally with the vibrator. The coupling positions are two places symmetrical with respect to the center of the vibrator. In such coupling positions, amplitude is large amplitude 0.97 times as large as maximum amplitude of the vibrator.

If the platform is coupled to the opening of the vibrator in positions where vibration in the (2, 1) mode is suppressed in the vibrator, vibration in the (2, 1) mode of the vibrator can be controlled by the platform.

To cause a substance to adhere or stick to the platform, for example, an absorptive material that can efficiently perform absorption of molecules may be added to the surface of the platform. As this absorptive material, there are global recognition materials and selective recognition materials. The global recognition materials are polymers that are not strong in selectivity but absorb a certain specific molecule group, for example, alcohol and ether. It is also effective to form these polymers as a nano-fiber or make these polymers porous to increase a surface area thereof. As recognition materials that are strong in selectivity, there are, for example, a material derived from an organism that causes the antigen-antibody reaction, a combination of an acceptor and a receptor, and a probe having a specific base sequence hybridizing with genes, DNAs, and RNAs. The recognition material may be a lipid double film.

In such a detection sensor, a substance as a detection object can be specific molecules or plural kinds of molecules having a specific property or characteristic. Consequently, this detection sensor can be used in, for example, a gas detection sensor, a smell sensor, and the like. For this purpose, when the detection sensor is a detection sensor that detects, as specific molecules, molecules derived from a gas and a living organism, floating molecules in a living space, volatile molecules, and the like, it is desirable to highly selectively detect only a specific kind of molecules. It is also possible to recognize plural kinds of molecules and expand an application range of uses using plural detection sensors having high selectivity. It is also possible to perform detection of a molecule group having a specific characteristic, a molecule group having the same side chain, and the like called global recognition. In this case, by using plural detection sensors, recognition of a molecule group may be performed from a difference in detection ability among the plural detection sensors according to signal processing, processing performed by using software, and the like. The configuration may be changed to operate in liquid and detect specific protein, enzyme, sugar chain, and the like.

Detection of very small mass can be used for bio-researches for a thickness monitor in forming a thin film, the antigen-antibody reaction, protein absorbing action, and the like. The detection sensor of the present invention is suitable for such uses.

It is also conceivable to use the detection sensor and the vibrator of the present invention for uses such as a small, stable, and highly sensitive gas sensor for home use and personal use and a disposable sensor excellent in portability and perform detection of hazardous substances floating in the air. If improvement of sensitivity further progresses, the application range is further expanded and can be developed to make it possible to detect and identify "smell". The use of the detection sensor of the present invention for uses other than the above is not prevented.

Moreover, in the detection sensor of the present invention, since so-called Si single crystal is used as a structural material, it is possible to manufacture the detection sensor with the MEMS technology. Therefore, it is also possible to incorporate the detection sensor in a chip identical with that of an Si semiconductor is formed. In that case, an extremely inexpensive and high performance detecting device for micro-substances can be realized.

According to the present invention, since the platform is added to and provided in the vibrator, when a substance adheres or sticks onto the platform, it is as if the substance concentratedly adheres or sticks to a region where the platform is connected in the vibrator. Therefore, the detection sensor can perform highly sensitive detection of a substance having mass and detection of the mass. Such a platform can also be formed integrally with the vibrator by using a semiconductor machining process or the like. Therefore, the platform can be formed at low cost.

Figure 1A:
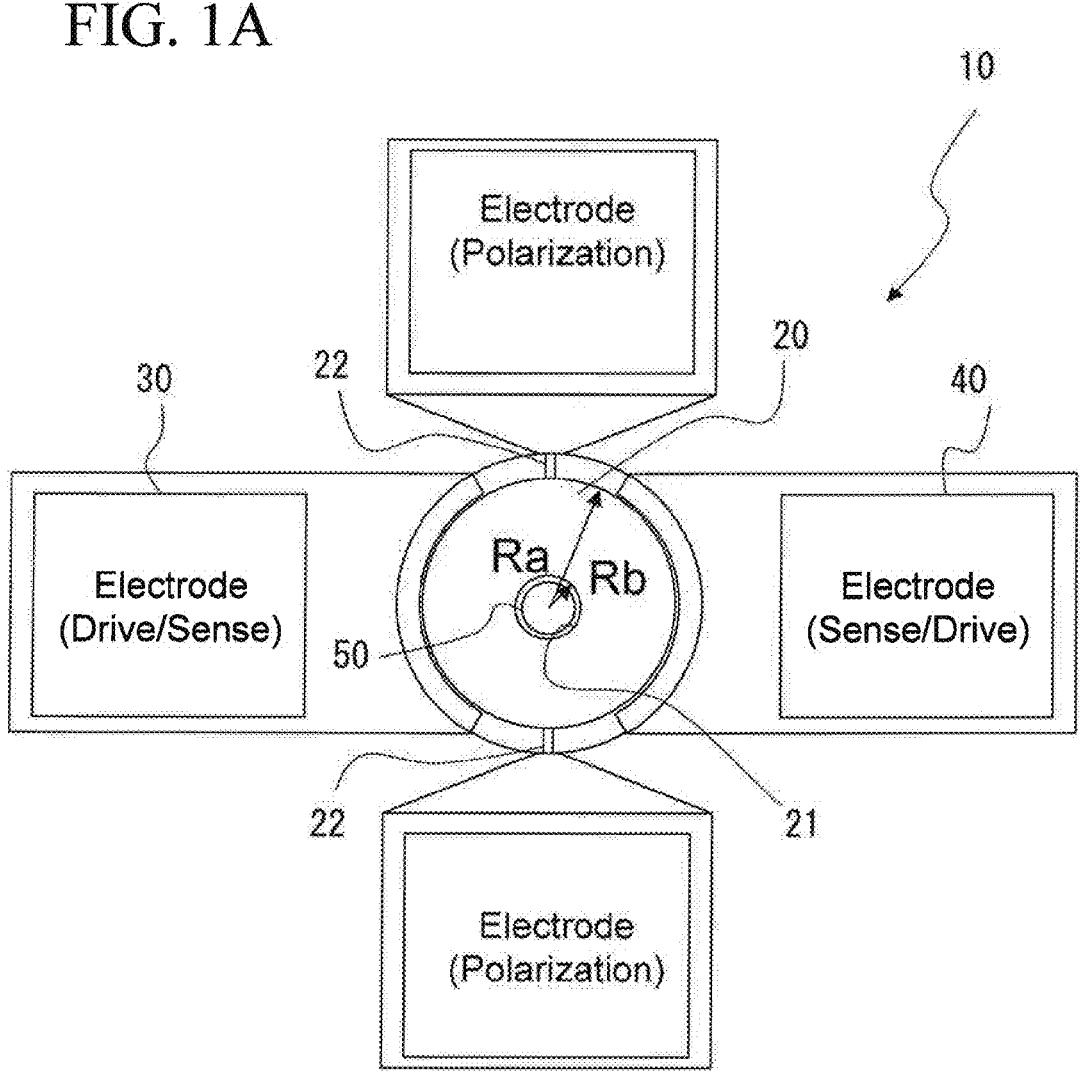
FIG. 1 is a diagram showing the structure of a sensor according to this embodiment.

DESCRIPTION OF SYMBOLS 10 sensor (detection sensor)
20 vibrator
21 opening
22 supporting members
40 detection unit
50 platform
51 bridges

BEST MODE FOR CARRYING OUT THE INVENTION

The present invention will be hereinafter explained in detail on the basis of an embodiment shown in the attached drawings.

Figure 1B:
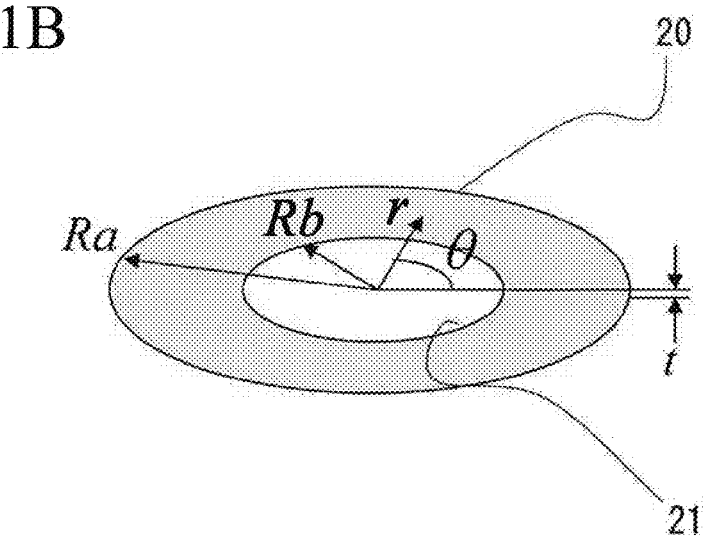

FIG. 1 is a diagram for explaining the basis structure of a sensor (a detection sensor) 10 in this embodiment.

The sensor 10 shown in FIG. 1 is disc-like and has a circular shape, a rectangular shape, or other shapes as a whole as appropriate. The sensor 10 includes an vibrator 20, a vibration frequency of which changes when a detection object such as a molecule having mass adheres thereto, a driving source 30 for causing the disc-like vibrator 20 to vibrate, and a detection unit 40 that detects a change in a vibration property in the vibrator 20.

The driving source 30 causes, using an electrostatic effect or a piezoelectric effect, the vibrator 20 to vibrate with an electric current generated by a not-shown controller on the outside.

The detection unit 40 detects vibration in the vibrator 20 using the electrostatic effect or the piezoelectric effect and outputs the vibration as an electric signal. At this point, when a substance having mass adheres to the vibrator 20, a frequency of the vibrator 20 changes being affected by the mass. The detection unit 40 can detects presence or absence of adhesion of a substance to the vibrator 20 or an amount of adhesion of a substance to the vibrator 20 by monitoring vibration outputted from the vibrator 20.

In such a sensor 10, an opening 21 is formed in the center of the vibrator 20. This vibrator 20 is supported by only supporting members 22 connected to predetermined positions in an outer peripheral portion and all remaining other portions are set in a free state.

An outer diameter of the vibrator 20 is represented as Ra and a diameter of the opening 21 is represented as Rb. It is preferable to set, in the vibrator 20, the outer diameter Ra of the vibrator 20 and the diameter Rb of the opening 21 (an inner diameter of the vibrator 20) such that Rb/Ra substantially satisfies a condition described below.

Vibration that occurs in the disc-like vibrator 20 includes three kinds of modes: (a) a Radial mode (a mode in which the vibrator 20 vibrates only in a radial direction (an r direction)), (b) a Tangential mode (a mode in which the vibrator 20 vibrates only in a θ direction), and (c) a Compound mode (a mode in which the vibration in the radial direction and the vibration in the θ direction are combined).

A formula for determining a resonance frequency in the Compound mode in the vibrator 20 is as indicated by the following formula (4):

[Formula 4]

$$f(K) = \begin{vmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{vmatrix} = 0 \quad (4)$$

where, $a_{11}$ to $a_{44}$ are defined as follows:

[Formula 5]

$a_{11} = -J_n(K)[(K\xi)^2/2 - n(n+1) + M_n(K)]$, $a_{12} = nJ_n(K\xi)[M_n(K\xi) - (n+1)]$ $a_{13} = -Y_n(K)[(K\xi)^2/2 - n(n+1) + N_n(K)]$, $a_{14} = nY_n(K\xi)[N_n(K\xi) - (n+1)]$ $a_{21} = -J_n(L)[(L\xi)^2/2 - n(n+1) + M_n(L)]$, $a_{22} = nJ_n(L\xi)[M_n(L\xi) - (n+1)]$ $a_{23} = -Y_n(L)[(L\xi)^2/2 - n(n+1) + N_n(L)]$, $a_{24} = nY_n(L\xi)[N_n(L\xi) - (n+1)]$ $a_{31} = -nJ_n(K)[M_n(K) - (n+1)]$, $a_{32} = J_n(K\xi)[(K\xi)^2/2 - n(n+1) + M_n(K\xi)]$ $a_{33} = -nY_n(K)[N_n(K) - (n+1)]$, $a_{34} = Y_n(K\xi)[(K\xi)^2/2 - n(n+1) + N_n(K\xi)]$ $a_{41} = -nJ_n(L)[M_n(L) - (n+1)]$, $a_{42} = J_n(L\xi)[(L\xi)^2/2 - n(n+1) + M_n(L\xi)]$ $a_{43} = -nY_n(L)[N_n(L) - (n+1)]$, $a_{44} = Y_n(L\xi)[(L\xi)^2/2 - n(n+1) + N_n(L\xi)]$ (5)

Where $K = hR_a$, $L = hR_b$, $M_n(x) = xJ_{n-1}(x)/J_n(x)$, $N_n(x) = xY_{n-1}(x)/Y_n(x)$ $\xi = \sqrt{2/(1-\sigma)}$, $h = \omega\sqrt{\rho(1-\sigma^2)/E}$ where, σ is a Poisson's ratio of a vibrator material, E is a Young's modulus of the vibration material, ρ is the density of the vibration material, and ω is an angular frequency ($=2\pi f$).

It is seen that, in two boundaries in the vibrator 20 having the opening 21, i.e., an outer diameter portion and an inner diameter portion, since the vibrator 20 is under a Free-Free condition, a residual stress in a Radial direction and a residual stress in a Tangential direction are eliminated, whereby four boundary conditions are decided. Displacement U(r, θ) in the Radial direction and displacement V(r, θ) in the Tangential direction, which are mode functions, can be represented by the following formula:

[Formula 6]

$$U(r,\theta) = \begin{bmatrix} A_5 \frac{\partial}{\partial r} J_n(hr) + A_6 \frac{n}{r} J_n(kr) + \\ A_7 \frac{\partial}{\partial r} Y_n(hr) + A_8 \frac{n}{r} Y_n(kr) \end{bmatrix} \cos n\theta \quad (6)$$

$$V(r,\theta) = \begin{bmatrix} A_5 \frac{n}{r} J_n(hr) + A_6 \frac{\partial}{\partial r} J_n(kr) + \\ A_7 \frac{n}{r} Y_n(hr) + A_8 \frac{\partial}{\partial r} Y_n(kr) \end{bmatrix} \sin n\theta$$

Where $$h = \omega \sqrt{\frac{\rho(1-\sigma^2)}{E}},$$

$$k = \omega \sqrt{\frac{\rho(2+2\sigma)}{E}},$$

$$k = h \sqrt{\frac{2}{1-\sigma}}$$

The following relational expression is calculated by applying the four boundary conditions described above to this formula (6):

[Formula 7]

$$\begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix} \begin{bmatrix} A_5 \\ A_6 \\ A_7 \\ A_8 \end{bmatrix} = 0 \quad (7)$$

The formula for determining a resonance frequency of formula (3) means that formula (7) holds in any $A_5$, $A_6$, $A_7$, and $A_8$. This is on condition that Determinant of a 4×4 matrix of formula (7) is 0. This is the formula (3) for determining a resonance frequency.

Coefficients $A_5$, $A_6$, $A_7$, and $A_8$ of formula (6), which are mode functions, are not yet decided. Unless the coefficients are not determined, a vibration state of the vibrator 20 is not set. Under a resonance condition, formula (7) holds in any $A_5$, $A_6$, $A_7$, and $A_8$. Therefore, the coefficients $A_5$, $A_6$, $A_7$, and $A_8$ during resonance are undecided and cannot be determined in this state. However, the matrix of formula (7) is resolved into linear equations and represented as indicated by the following formula (8):

[Formula 8]

$$a_{11}A_5 + a_{12}A_6 + a_{13}A_7 + a_{14}A_8 = 0$$

$$a_{21}A_5 + a_{22}A_6 + a_{23}A_7 + a_{24}A_8 = 0$$

$$a_{31}A_5 + a_{32}A_6 + a_{33}A_7 + a_{34}A_8 = 0$$

$$a_{41}A_5 + a_{42}A_6 + a_{43}A_7 + a_{44}A_8 = 0 \quad (8)$$

Arbitrary three equations are extracted out of four linear equations of formula (8) calculated in this way. A coefficient can be decided as a ratio to any one of the coefficients $A_5$, $A_6$, $A_7$, and $A_8$ in the three equations. For example, when upper three equations are extracted from formula (8) and all of the equations are divided by $A_5$, a simultaneous linear equation as indicated by the following formula (9) is obtained:

[Formula 9]

$$a_{11} + a_{12} \frac{A_6}{A_5} + a_{13} \frac{A_7}{A_5} + a_{14} \frac{A_8}{A_5} = 0 \quad (9)$$

$$a_{21} + a_{22} \frac{A_6}{A_5} + a_{23} \frac{A_7}{A_5} + a_{24} \frac{A_8}{A_5} = 0$$

$$a_{31} + a_{32} \frac{A_6}{A_5} + a_{33} \frac{A_7}{A_5} + a_{34} \frac{A_8}{A_5} = 0$$

Coefficient ratios $A_6/A_5$, $A_7/A_5$, and $A_8/A_5$ with $A_5$ set as a denominator can be calculated from this formula (9). If this result is substituted in formula (6), all displacements in the Radial direction and the Tangential direction during resonance, i.e., mode functions can be determined. The upper three equations of formula (8) are used here. However, the formula (8) can be solved in the same manner by using arbitrary different three equations. Four sets of different simultaneous linear equations are obtained here. However, all the calculated results are the same.

Since all the simultaneous linear equations are in a proportional relation with respect to $A_5$, the mode functions do not essentially change even if $A_5$ is set to 1. Therefore, if $A_5$ is set to 1 again and an r component in the Radial direction in respective modes is represented as U(r) and an r component in the Tangential direction is represented as V(r), the mode functions of formula (6) are changed as indicated by the following formula (10):

[Formula 10]

$$U(r,\theta) = U(r) \cos n\theta$$

$$V(r,\theta) = V(r) \sin n\theta \quad (10)$$

where, U(r) and V(r) are as indicated by the following formula (11):

[Formula 11]

$$U(r) = \frac{\partial}{\partial r} J_n(hr) + A_6 \frac{n}{r} J_n(kr) + A_7 \frac{\partial}{\partial r} Y_n(hr) + A_8 \frac{n}{r} Y_n(kr) \quad (11)$$

$$V(r) = \frac{n}{r} J_n(hr) + A_6 \frac{\partial}{\partial r} J_n(kr) + A_7 \frac{n}{r} Y_n(hr) + A_8 \frac{\partial}{\partial r} Y_n(kr)$$

This analysis is an analysis for the disc-like vibrator 20 of a circular shape having the opening 21 unlike a normal disc-like vibrator. In this vibrator 20, U(r) and V(r) shown in formula (11) substantially change according to a ratio of the outer diameter Ra and the inner diameter Rb of this vibrator 20. When the ratio of the outer diameter Ra and the inner diameter Rb of the vibrator 20 reaches a specific value, it is possible that U(r) or V(r) is 0.

For example, when U(Ra) is 0 in the outer diameter Ra of the vibrator 20, vibration in an outer diameter portion of the vibrator 20 is eliminated. Therefore, the vibrator 20 is supported in the outer diameter portion by the supporting members 22.

Figure 10:
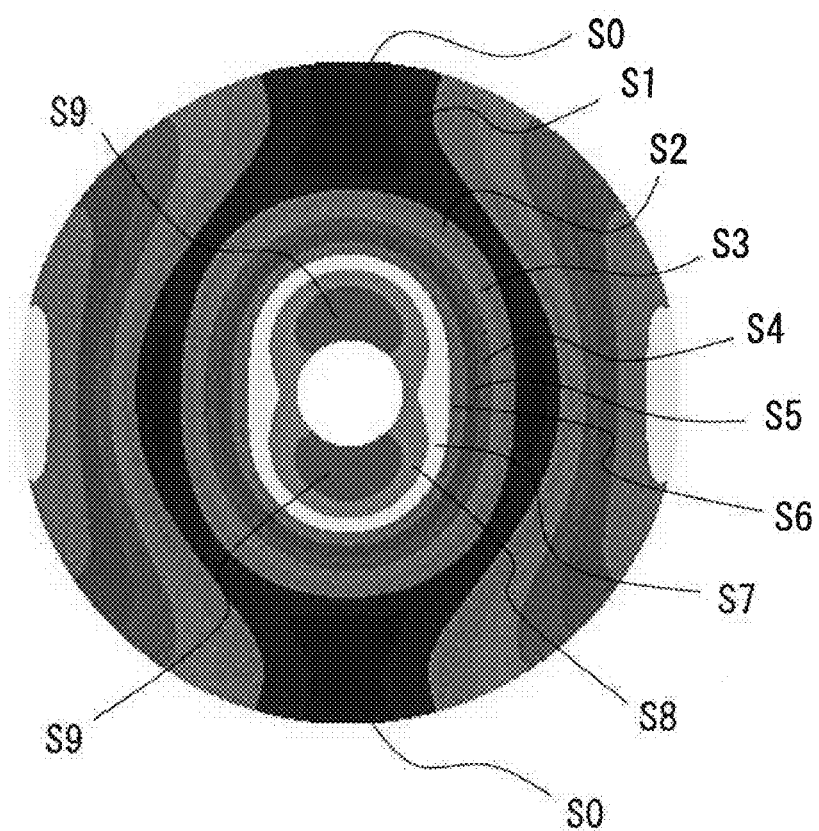
FIG. 10 is a diagram showing a distribution of amplitudes of the disc-like vibrator in the (1, 2) mode.

In this case, even if V(RA)≠0, displacement in the Tangential direction is obtained by multiplying (integrating) V(Ra) with sin(nθ) as shown in FIG. 10. Therefore, vibration does not occur with V(r, θ) of formula (10) in positions where sin(nθ) is 0. In the case of a vibration mode of n=1, if the vibrator 20 is held by the supporting members 22 in positions of V(Ra, 0) and V(Ra, π), vibration energy of the vibrator 20 is not lost through the supporting members 22.

Conversely, in the case of V(Ra)=0, even if U(Ra) is not 0, displacement in the Radial direction is obtained by multiplying U(Ra) with cos(nθ). Therefore, the vibrator 20 only has to be held in a position where cos(nθ) is 0.

A method of holding the disc-like vibrator 20 with a hole in the outer diameter portion thereof is described above. However, even when the vibrator 20 is held in inner diameter portion thereof, positions of the inner diameter portion to be held can be determined by the same idea.

FIGS. 2 to 4 illustrate states of fluctuation in r components, i.e., U(r) and V(r) shown in formula (11) in respective vibration modes of n=1 to n=3, respectively, with a ratio Rb/Ra of the inner diameter Rb and the outer diameter Ra plotted on the abscissa. In this case, an Si single crystal is assumed as a material of the vibrator 20 and the Poisson's ratio σ is set to 0.28. In the figures, n indicates a modal number of a vibration mode and m indicates an order of harmonic vibration.

In FIGS. 2 to 4, a resonance frequency of a lowest order (m=1) to a fourth resonance frequency (m=4) are shown in the respective mode. This is shown as (n, m) according to a normal mode representation.

Figure 2A:
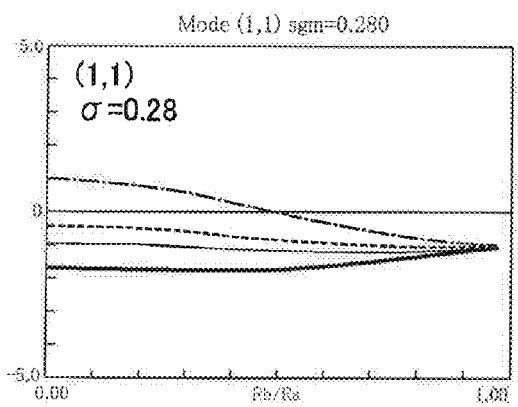
FIG. 2 is a diagram showing a relation between a ratio of an outer diameter and an inner diameter of a disc-like vibrator and values of U(Ra), U(Rb), V(Ra), and V(Rb) in an n=1 mode.
Figure 2B:
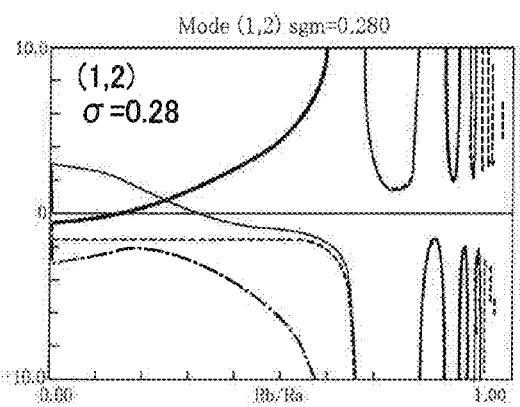
Figure 2C:
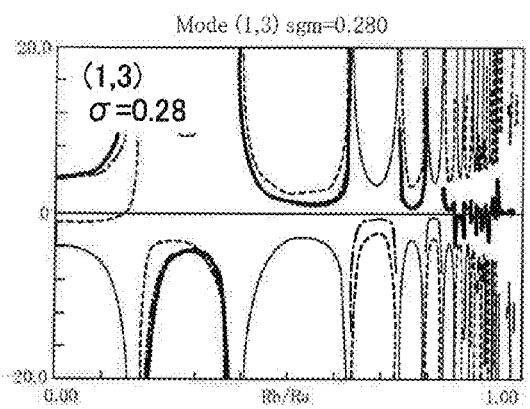
Figure 2D:
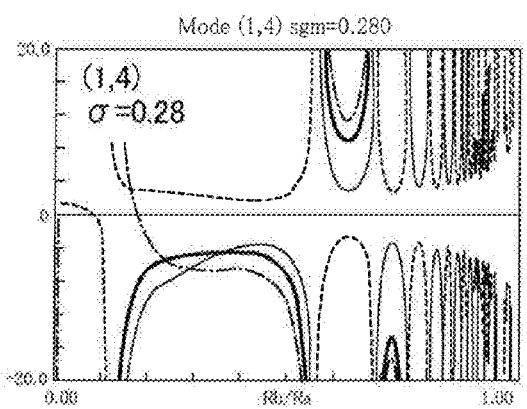
Figure 3A:
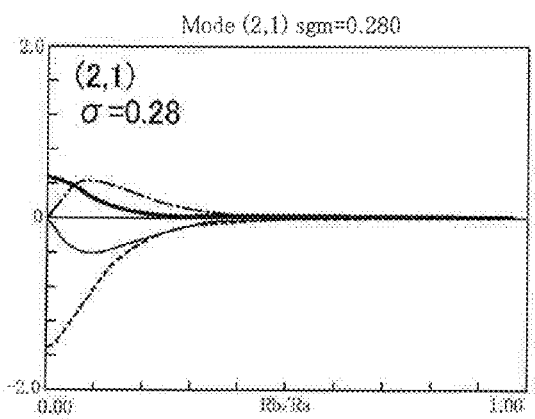
FIG. 3 is a diagram showing a relation between the ratio of the outer diameter and the inner diameter of the disc-like vibrator and values of U(Ra), U(Rb), V(Ra), and V(Rb) in an n=2 mode.
Figure 3B:
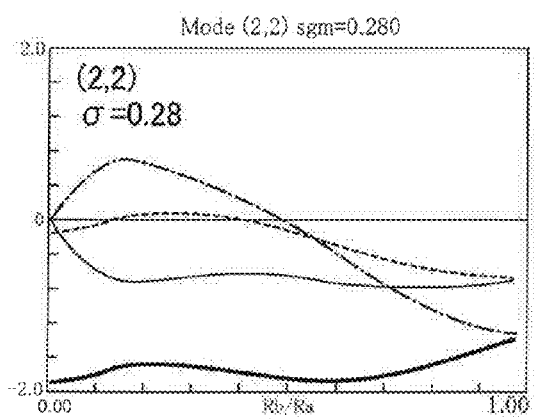
Figure 3C:
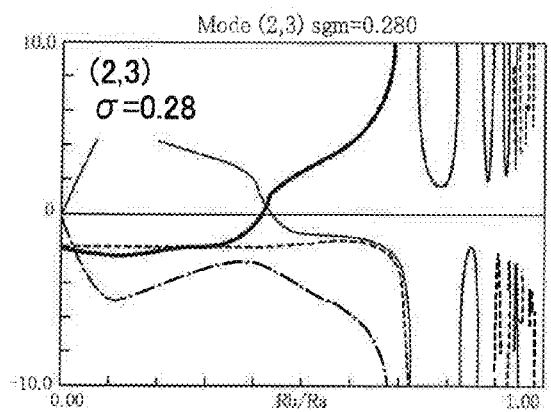
Figure 3D:
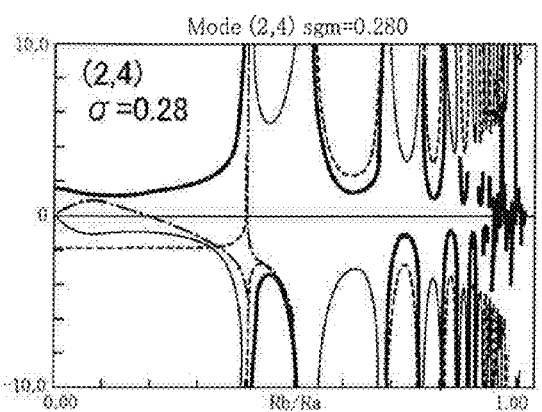
Figure 4A:
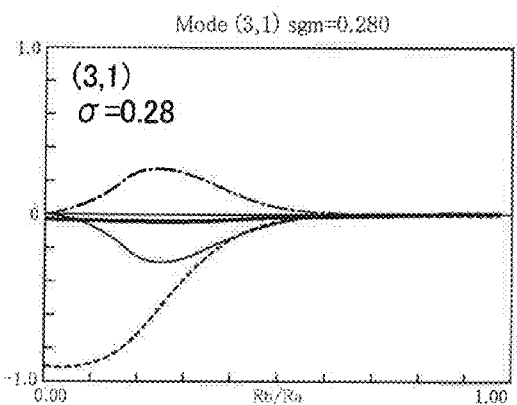
FIG. 4 is a diagram showing a relation between the ratio of the outer diameter and the inner diameter of the disc-like vibrator and values of U(Ra), U(Rb), V(Ra), and V(Rb) in an n=3 mode.
Figure 4B:
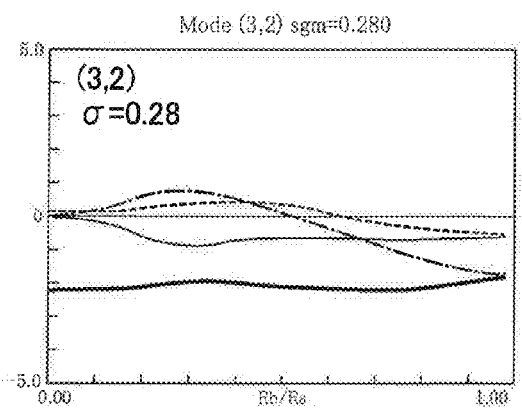
Figure 4C:
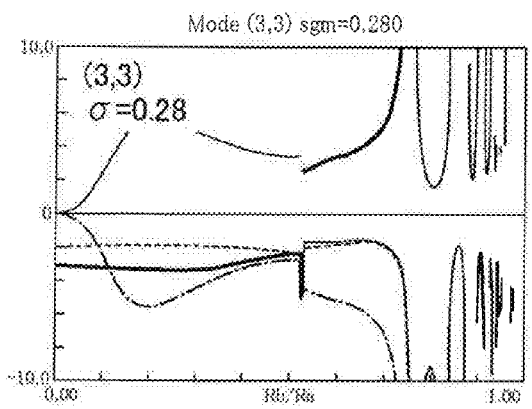
Figure 4D:
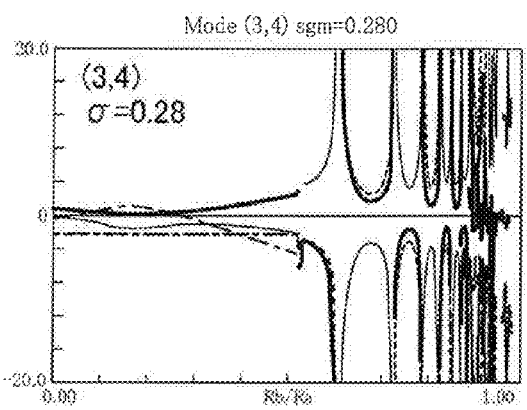
Figure 5A:
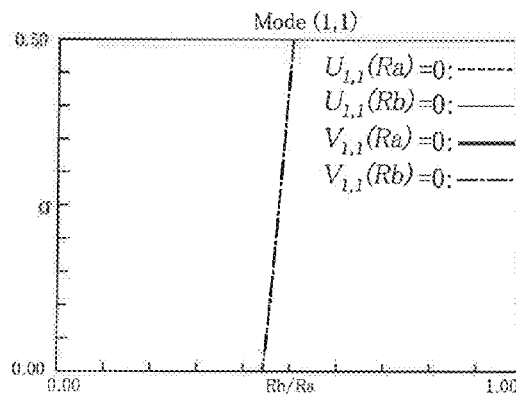
FIG. 5 is a diagram showing a relation between the ratio of the outer diameter and the inner diameter of the disc-like vibrator and a Poisson's ratio at the time when formula (12) holds in the n–1 mode.
Figure 5B:
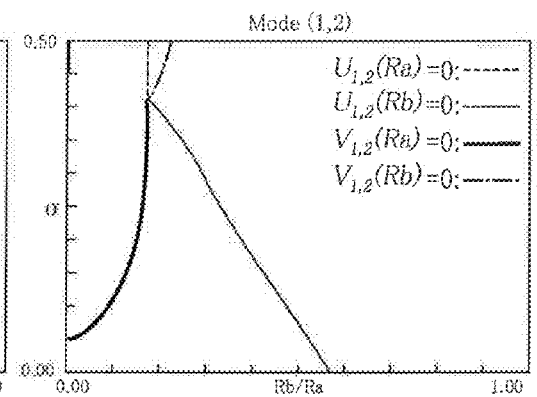
Figure 5C:
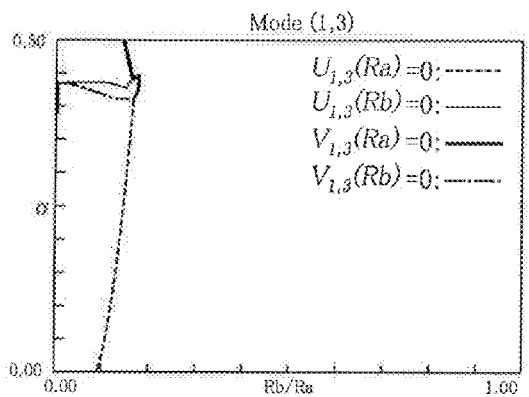
Figure 5D:
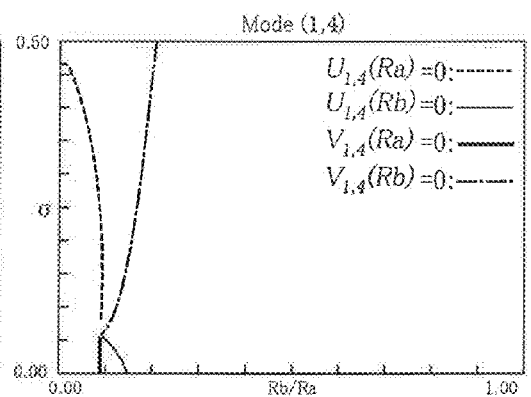
Figure 6A:
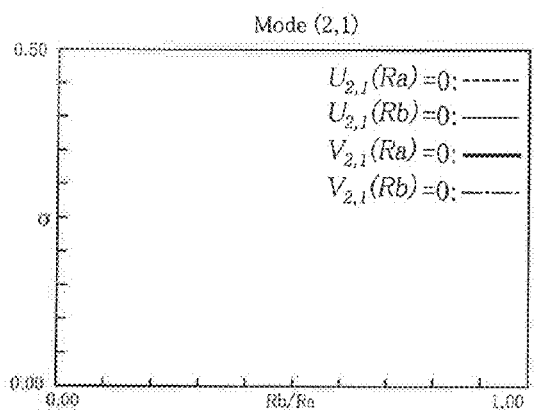
FIG. 6 is a diagram showing a relation between the ratio of the outer diameter and the inner diameter of the disc-like vibrator and the Poisson's ratio at the time when formula (12) holds in the n=2 mode.
Figure 6B:
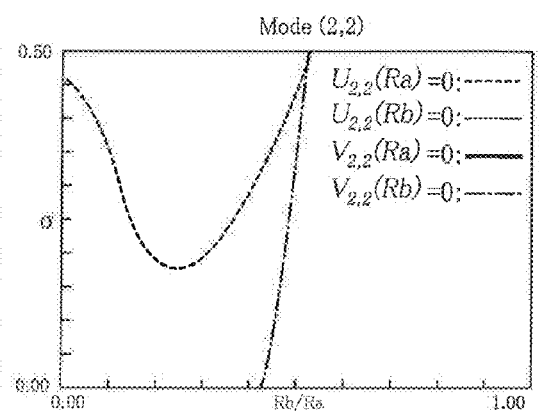
Figure 6C:
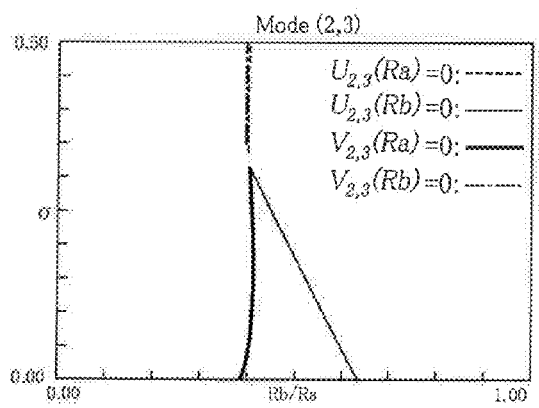
Figure 6D:
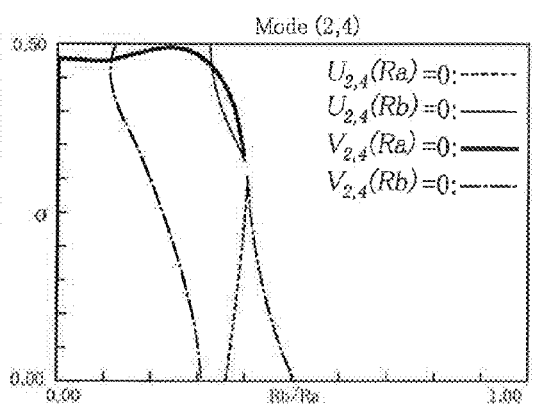

Looking at FIGS. 2 to 4, it is observed that any one of U(Ra), U(Rb), V(Ra), and V(Rb) is 0 at appropriate Rb/Ra except in a (2, 1) mode in FIG. 3A and a (3, 1) mode in FIG. 4A.

For example, in a (1, 2) mode shown in FIG. 2B, it is indicated that V(Ra) is 0 at Rb/Ra=0.17. Therefore, to design the vibrator 20 used in the (1, 2) mode using a material (e.g., single crystal Si) having a Poisson's ratio of 0.28, if a ratio of the inner diameter Rb and the outer diameter Ra is selected to 0.17 and the vibrator 20 is designed to be held in positions at an angle of cos θ=0, i.e., θ=±π/2 in the inner diameter portion, it is possible to hold the vibrator 20 without affecting resonant vibration of the vibrator 20 at all.

In other words, in the case of the vibrator 20 having the outer diameter Ra of 100 μm and used in the (1, 2) mode, Rb/Ra is 0.17 when a diameter of the opening 21 is set to 17 μm and vibration in the Tangential direction in the outer diameter portion of the vibrator 20 can be reduced to 0. In this case, a method of holding the vibrator 20 without affecting resonant vibration at all can be realized by supporting the vibrator 20 in the positions at the angle of cos θ=0, i.e., θ=±π/2 in the outer diameter portion of the opening 21.

In a general material, for example, a material having the Poisson's ratio σ of 0 to 0.5, it is extremely important to check in which Rb/Ra a case in which U(Ra), U(Rb), V(Ra), and V(Rb) are 0 occurs. The inventors checked combinations of Rb/Ra and the Poisson's ratio σ, with which the following formula (12) holds, for respective modes (n=1 to 3 and m=1 to 4) from formula (11).

[Formula 12]

$$U(Ra) = \frac{\partial}{\partial r}J_n(hr) + A_6\frac{n}{r}J_n(kr) + A_7\frac{\partial}{\partial r}Y_n(hr) + A_8\frac{n}{r}Y_n(kr)\bigg|_{r=Ra} = 0 \quad (12)$$

$$U(Rb) = \frac{\partial}{\partial r}J_n(hr) + A_6\frac{n}{r}J_n(kr) +$$
$$\quad\quad\quad\quad A_7\frac{\partial}{\partial r}Y_n(hr) + A_8\frac{n}{r}Y_n(kr)\bigg|_{r=Rb} = 0$$

$$V(Ra) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)\bigg|_{r=Ra} = 0$$

$$V(Rb) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)\bigg|_{r=Rb} = 0$$

Results of the check are shown in FIGS. 5 to 7.

All materials are regarded as being checked by setting only the Poisson's ratio as a variable because, from formula (6), h and k have a relation $k=h(2/(1-\sigma))^{1/2}$ and, when h and k are regarded as variables, the two variables are associated with each other by only the Poisson's ratio σ.

In FIGS. 5 to 7, relations between the Poisson's ratio σ (the ordinate) and the ratio Rb/Ra of the inner diameter Rb and the outer diameter Ra of the vibrator 20 (the abscissa) that satisfy formula (12) in the respective modes of n=1 to 3 and m=1 to 4 are shown. In other words, if a Poisson's ratio of a vibrator material is known, from the relations shown in FIGS. 5 to 7, it is possible to determine a vibration mode, positions where the vibrator 20 is held, and a ratio of the inner diameter Rb and the outer diameter Ra of the vibrator 20. A resonance frequency is determined by changing, for example, a size, i.e., the outer diameter Ra of the vibrator 20.

In this way, it is possible to realize, by learning the relations shown in FIGS. 5 to 7 in advance, the disc-like vibrator 20 having high performance in which vibration energy does not escape through the holding unit.

In the case of the vibrator 20 used by being caused to vibrate in the Tangential direction, it is preferable that the supporting members 22 are supporting members having length $L_R$ indicated by the following formula (13). When a driving system employing the piezoelectric effect is adopted in the driving source 30, the vibrator 20 is used by being caused to vibrate in the Tangential direction. Therefore, in this case, it is preferable that the length of the supporting members 22 is set to $L_R$ represented by formula (13):

[Formula 13]

$$L_R = \frac{n_m\pi}{2\omega}\sqrt{\frac{E}{\rho}}, n_m = 1, 3, 5 \ldots \quad (13)$$

In the case of the vibrator 20 used by being caused to vibrate in the Radial direction, it is preferable that the supporting members 22 are supporting members having length Ls indicated by the following formula (14):

[Formula 14]

$$L_s = \frac{n_m \pi}{2\omega} \sqrt{\frac{KE}{\rho(2+2\sigma)}}, n_m = 1, 3, 5 \ldots \quad (14)$$

Where $$K = \frac{10(1+\sigma)}{12+11\sigma}$$

By appropriately selecting the ratio Rb/Ra of the inner diameter Rb and the outer diameter Ra of the vibrator 20, U(Ra) or U(Rb), which is an r component of displacement in the Radial direction in the outer diameter portion or the inner diameter portion of the vibrator 20, and V(Ra) or V(Rb), which is an r component of displacement in the Tangential direction, may be 0. By using such a phenomenon peculiar to the disc-like vibrator 20 having the opening 21, it is possible to hold the vibrator 20 without affecting resonant vibration of the vibrator 20 at all and provide the vibrator 20 having extremely high Q.

Figure 8:
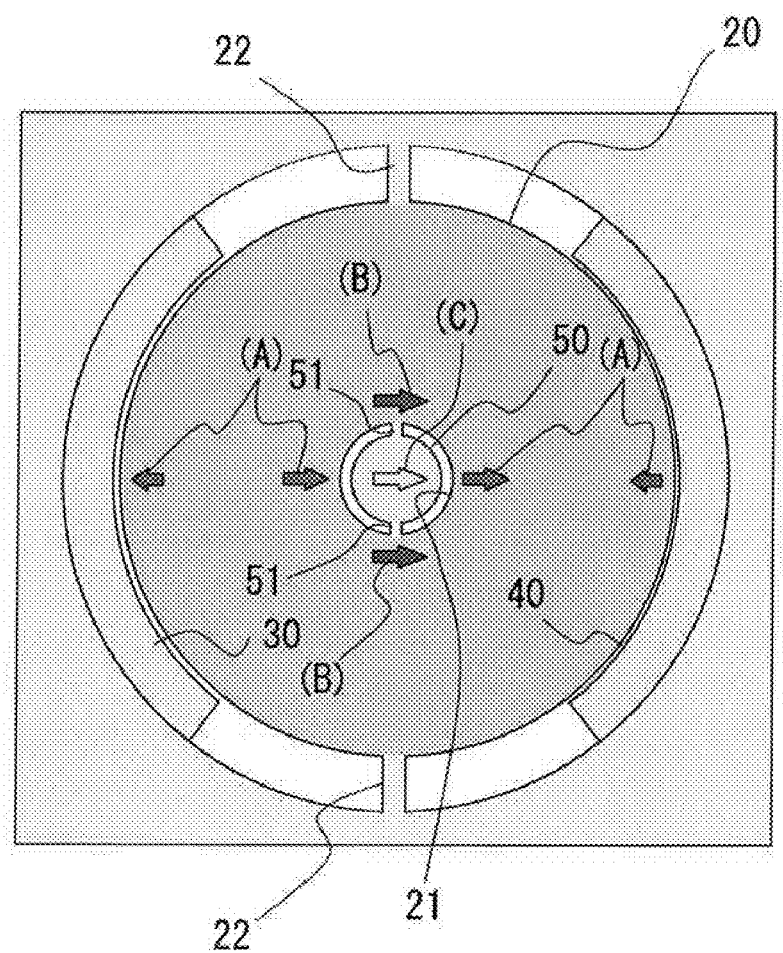
FIG. 8 is a diagram showing an example of the structure in which a platform is provided in the disc-like vibrator in a (1, 2) mode.

Moreover, as shown in FIG. 8, in the present invention, a platform 50 is formed in the opening 21 of the vibrator 20. This platform 50 is, for example, a disc-like and an outer peripheral portion thereof is connected to and supported in an inner diameter portion of the opening 21 of the vibrator 20 by bridges 51.

In this case, as described in detail later, the platform 50 is connected to, via the bridges 51, places where the platform 50 vibrates integrally with the vibrator 20.

To cause the platform 50 to behave integrally with the vibrator 20, it is preferable to mechanically couple, via the bridges 51, the platform 50 to regions where vibration occurs only in one of an r direction and a θ direction in the vibrator 20.

In this case, the bridges 51 are provided in one or more places but may be provided in two or more places. In this case, to prevent unnecessary distortion from being caused in the platform 50, i.e., to prevent an unnecessary loss from being given to the vibrator 20 by the addition of the platform 50, it is preferable that amplitudes of the vibrator 20 in the places where the bridges 51 are provided are equal. Therefore, it is advisable to provide the bridges 51 in two or more places line-symmetrical or point-symmetrical with respect to the center of the vibrator 20.

Consequently, it is possible to cause the platform 50 to behave in the r direction or the θ direction integrally with the vibrator 20 according to a vibration mode of the vibrator 20 and connection places by the bridges 51.

It is preferable that regions where the platform 50 is connected to the vibrator 20 via the bridges 51 are regions where vibration amplitude is as large as possible in the vibrator 20. Consequently, it is possible to more highly sensitively detect the influence of the mass of a substance on the platform 50 transmitted to the vibrator 20 via the platform 50 and the bridges 51.

The platform 50 is formed such that a resonance frequency thereof is higher than a resonance frequency of the vibrator 20. Consequently, it is possible to prevent the platform 50 from being excited by the vibrator 20. Moreover, it is preferable to form the bridges 51 as short as possible. This is because, as the bridges 51 is longer, the bridges 51 are more excited by the vibration of the vibrator 20 and it is likely that a component of the vibration is transmitted to the platform 50.

The platform 50 and the bridges 51 may be formed of any material. However, when easiness of manufacturing is taken into account, it is preferable to form the platform 50 and the bridges 51 with the same material as the vibrator 20. In that case, it is preferable to form, for example, the vibrator 20, the platform 50, and the bridges 51 in an identical layer with a semiconductor machining technique such as the photolithography method. It goes without saying that the present invention does not exclude the structure in which the platform 50 and the bridges 51 are three-dimensionally formed with respect to the vibrator 20.

When the platform 50 and the vibrator 20 are formed of an identical material, to set a resonance frequency of the platform 50 higher than a resonance frequency of the vibrator 20, an external dimension of the platform 50 only has to be set smaller than the inner diameter Rb of the opening 21 of the vibrator 20. However, to cause substances to adhere or stick onto the platform 50 as many as possible, it is preferable to form the platform 50 as large as possible.

A position and the like of attachment of the platform 50 to the vibrator 20 described above are examined by using specific examples.

FIRST EXAMPLE

Figure 9:
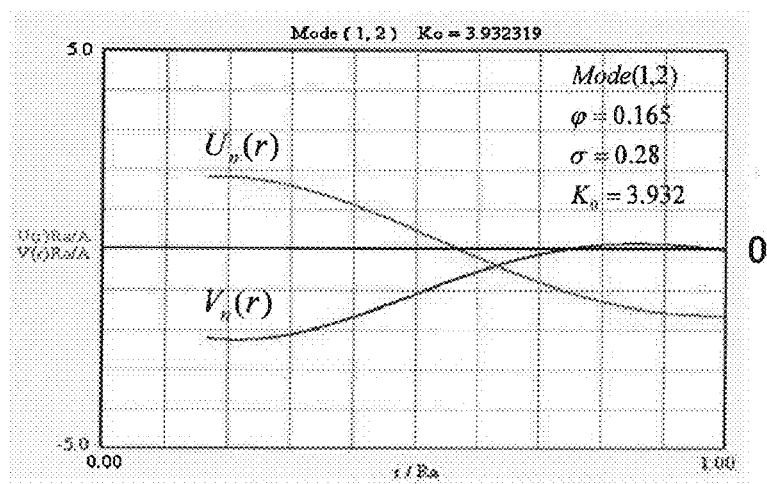
FIG. 9 is a diagram showing values of U(r) and V(r) in a position of a radius r of the disc-like vibrator in the (1, 2) mode.

A result obtained by calculating formula (11) concerning a case in which a material of the vibrator 20 is Si, for example, n=1 and m=2, i.e., the (1, 2) mode is selected, and φ=Rb/Ra=0.165 is FIG. 9. FIG. 10 shows a figure of the mode. In FIG. 10, magnitudes of vibration amplitudes on the vibrator 20 are shown by being sectioned into ten stages. A portion indicated by S0 is amplitude minimum (zero) and a portion indicated by S9 is amplitude maximum.

Un(r, θ) and Vn(r, θ) of formula (10) indicate displacements in the r direction and the θ direction, respectively. This calculation example indicates that, when r/Ra is 1, i.e., r is Ra, since $V_1$(Ra) is 0, in the outer diameter portion of the vibrator 20, the displacement in the θ is 0 no matter what θ is. Since a mode function $U_1$(r, θ) in the r direction is cos θ=0 at θ=π/2 or θ=3π/2, displacement in the r direction is also 0 in these positions.

In other words, in outer diameter positions of the vibrator 20 with φ=0.165, there is no vibration in positions at an angle θ=π/2 or θ=3π/2. Therefore, if the vibrator 20 is held in these positions, vibration energy is not lost through the holding unit.

Moreover, as it is seen from FIG. 10, in the vibrator 20 under this condition, the inner diameter portion of the vibrator 20 has large vibration amplitude at angles θ=π/2 and θ=3π/2. The vibrator 20 is held in a position where cos θ=0 because amplitude components in these positions are in positions at the angles θ=π/2 and θ=3π/2. Therefore, vibration components in these positions are not vibration of the r component but vibration of the θ component. Moreover, since sin π/2 is 1 and sin 3π/2 is −1, the vibrator 20 is vibrating in angle directions opposite to each other in these positions. In other words, as shown in FIG. 10, in a position (Rb, π/2) and a position (Rb, 3π/2) of the inner diameter portion of the vibrator 20 in the (1, 2) mode, both the vibrators 20 are vibrating in parallel to each other in a right or left direction in these positions.

FIG. 8 is an example that is created on the basis of these study results and in which the platform 50 is additionally provided in the opening 21 of the vibrator 20 that vibrates in the (1, 2) mode. In two places where θ is π/2 and θ is 3π/2 in the inner diameter portion of the vibrator 20, the platform 50 and the vibrator 20 are mechanically coupled by the bridges 51. In other words, the platform 50 is mechanically coupled to the vibrator 20 in two places that are symmetrical with respect to the center of the vibrator 20 and where vibration amplitude is large.

In this case, the platform 50 is in a state in which the platform is caused to vibrate in the horizontal direction by the θ component among vibration components of the vibrator 20. This state is also a state in which the platform 50 is caused to vibrate in a mode in which n is an odd number. In other words, when the platform 50 is formed in a size that satisfies a resonance condition of an odd number mode such as n=1, 3, 5, ..., a distribution of vibration amplitudes due to the mode appears in the platform 50. The platform 50 falls into a state inconvenient for use as the sensor 10. On the other hand, when the platform 50 is small and does not satisfy the resonance condition, the platform 50 can be regarded as a complete rigid body. The platform 50 uniformly vibrates in the horizontal direction. In this state, since the platform 50 performs uniformly vibration in the horizontal direction with large amplitude, the platform 50 is in a state convenient for use as the sensor 10.

In FIG. 8, arrows (A) and (B) indicate displacements in the r direction and the θ direction of the vibrator 20, respectively, and an arrow (C) indicates vibration of the platform 50. In this way, in a mode in which n is an odd number, the entire platform 50 can be caused to uniformly vibrate in a specific direction regardless of a value of m.

SECOND EXAMPLE

Next, an example in the case of n=2 is described. A result obtained by selecting a (2, 3) mode as a vibration mode of the vibrator 20 and calculating formula (11) with φ set to 0.41 is FIG. 11.

Figure 11:
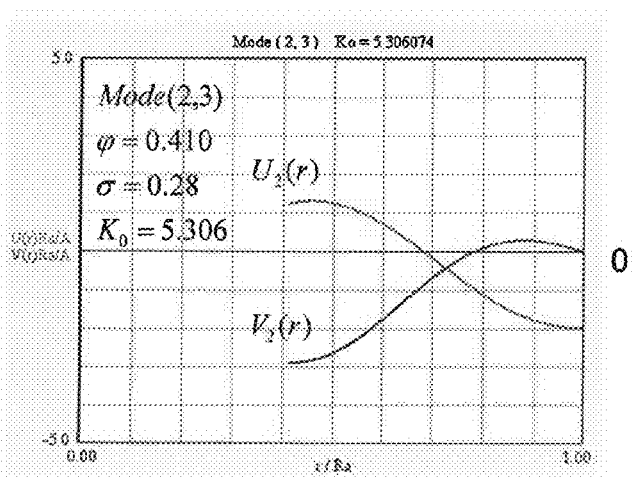
FIG. 11 is a diagram showing values of U(r) and V(r) in the position of the radius r of the disc-like vibrator in a (2, 3) mode.

As it is seen from FIG. 11, since $V_2(Ra)$ is 0 when r/Ra is 1, displacement in the θ direction is always 0 in an outer diameter portion of the vibrator 20. Moreover, since $U_2(r, θ)$, which is a mode function in the r direction, is $\cos 2θ=0$ at respective angles of $θ=π/4$, $θ=3π/4$, $θ=5π/4$, and $θ=7π/4$, displacement in the r direction at these angles is also 0. In other words, in the vibrator 20 with φ=0.410, there is no vibration at all in positions at the angles $θ=πn/4$, $θ=3π/4$, $θ=5π/4$, and $θ=7π/4$ in the outer diameter portion. Therefore, if the vibrator 20 is held in these positions, vibration energy is not lost through the holding unit. A mode figure of this example is shown in FIG. 12.

Figure 12:
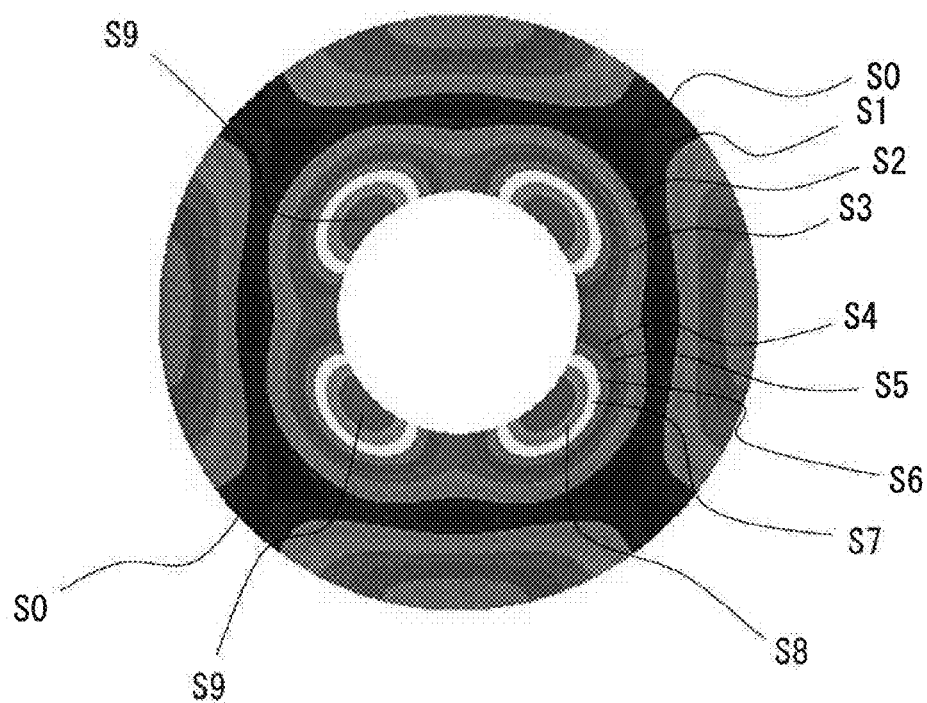
FIG. 12 is a diagram showing a distribution of amplitudes of the disc-like vibrator in the (2, 3) mode.

It is seen from this FIG. 12 that, in the (2, 3) mode, the vibrator 20 has large vibration amplitude in the positions at the angles $θ=π/4$, $θ=3π/4$, $θ=5π/4$, and $θ=7π/4$ near the inner diameter portion of the vibrator 20. Since this vibration component is $\cos 2θ=0$ in the positions at the angles $θ=π/4$, $θ=3π/4$, $θ=5π/4$, and $θ=7π/4$, the vibration component is not vibration of the r component but large vibration of the θ component. In the positions of $θ=π/4$ and $θ=5π/4$, since $\sin 2θ$ is 1, the vibration component is vibration in an identical angular direction. It is seen that, in the positions of $θ=3π/4$ and $θ=7π/4$, since $\sin 2θ$ is −1, the vibration component is vibration in an angular direction opposite to the case described above.

Figure 13:
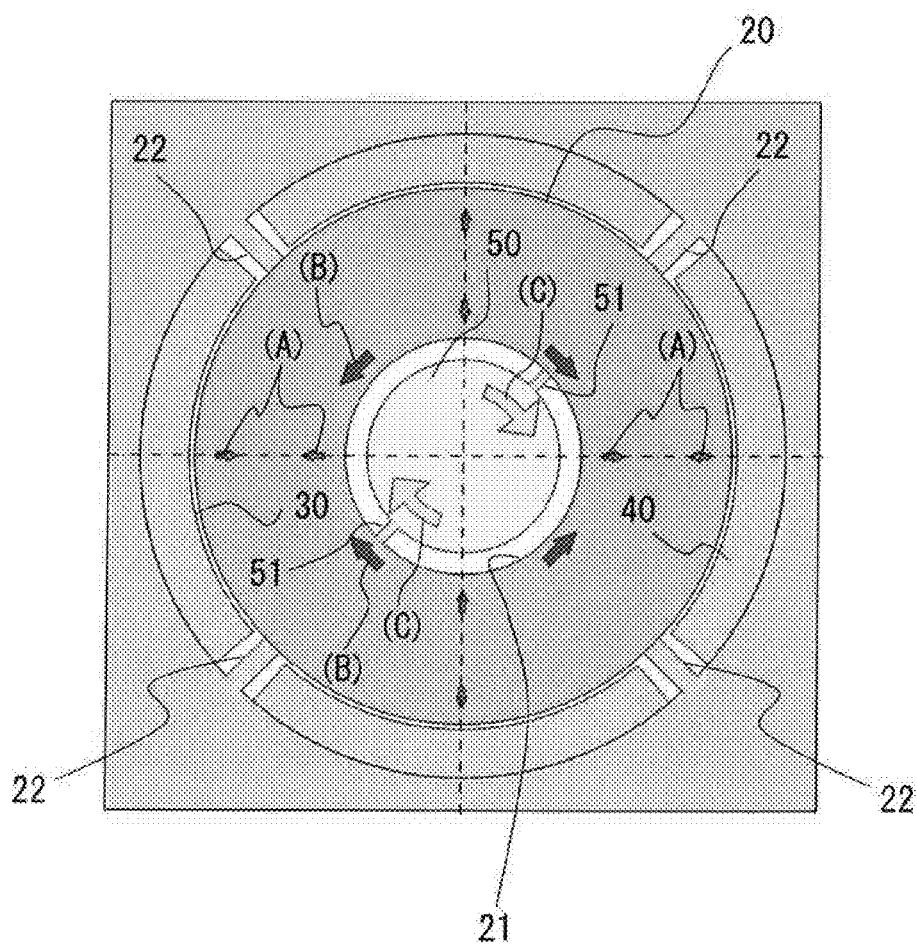
FIG. 13 is a diagram showing an example of the structure in which a platform is provided in a disc-like vibrator in the (2, 3) mode.

FIG. 13 is an example in which the platform 50 is provided in the opening 21 of the vibrator 20 in this (2, 3) mode and is an example in which the platform 50 and the vibrator 20 are mechanically coupled by the bridges 51 in two places in positions point-symmetrical with respect to the center of the vibrator 20, which vibrates in the (2, 3) mode, where vibration amplitude is large. In this case, the entire surface of the platform 50 vibrates in the θ direction with the θ component of the vibrator 20 in the (2, 3) mode. In this figure, arrows (A) and (B) indicate displacements in the r direction and the θ direction of the vibrator 20, respectively, and an arrow (C) indicates a state of the vibration of the platform 50.

As it is seen from FIG. 12, four places where vibration amplitude is large appear near the inner diameter portion of the vibrator 20 with a hole in the n=2 mode. When the vibrator 20 and the platform 50 are mechanically coupled in point-symmetrical two places among the four places or in all the four places, the platform 50 is excited in an even number order mode such as n=2, 4, ... (in the case of the two places or the four places) or a Pure Tangential Mode (in the case of two places). In this case, when the platform 50 satisfies excitation conditions of the even number order mode or the Pure Tangential Mode, the platform 50 vibrates in the even number order mode or the Pure Tangential Mode. A distribution of vibration amplitudes due to the mode is formed in the platform 50. When the platform 50 does not satisfy these conditions, if the platform 50 is mechanically coupled in the two places, the platform 50 performs uniform rotational vibration. However, if the platform 50 is mechanically coupled in the four places, vibration conditions of the vibrator 20 are substantially changed.

In this way, mechanical connection places of the vibrator 20 and the platform 50 in the n=2 mode are in two places with respect to the center of the vibrator. Alternatively, if the vibrator 20 can be surely held, the vibrator 20 and the platform 50 may be mechanically coupled in one place.

To put this in general, in an nth order vibration mode, since vibration in the same angular direction depends on $\sin(nθ)$ at θ=0 to 2π, regions where large vibration occurs only in the θ direction are n places. Therefore, the number of places suitable for performing mechanical coupling of the vibrator 20 including a perforated type and the platform 50 by the bridges 51 is equal to or smaller than n.

[Conditions in the Case in which the Platform 50 is Provided in the Opening 21 of the Vibrator 20]

As in the example of n=2 described above, in a mode in which n is an even number, the vibrator 20 and the platform 50 are mechanically coupled in two places point-symmetrical with respect to the center. In this case, when the platform 50 does not satisfy the vibration conditions of the even number order mode or the Pure Tangential Mode, the platform 50 always performs uniform rotational vibration regardless of a value of m. On the other hand, when the platform 50 is increased in size, the platform 50 satisfies the vibration conditions of the even number order mode or the Pure Tangential Mode and vibrates in a mode that satisfies the vibration conditions. The platform 50 vibrates according to an amplitude distribution determined by a mode function of the mode. In this way, the entire surface of the platform 50 mechanically coupled to the vibrator 20 in the two places does not always uniformly vibrate.

For example, when a resonance frequency of the platform 50 is higher than a vibration frequency of the vibrator 20, the platform 50 does not resonantly vibrate. The platform 50 changes to a complete rigid body and performs uniform vibration according to the vibration of the coupling portion of the vibrator 20.

Figure 14:
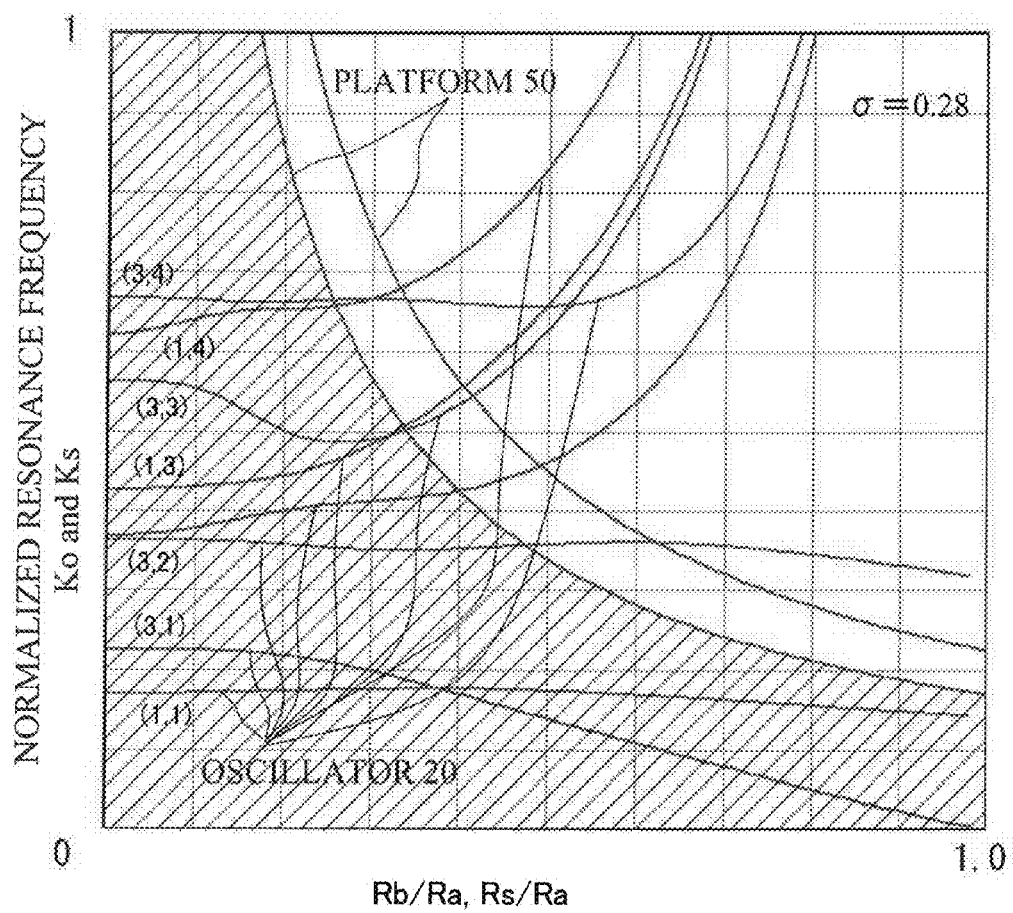
FIG. 14 is a diagram showing a relation between a resonance frequency of the vibrator and an inner diameter Rb and an outer diameter Ra of the vibrator and a relation between a resonance frequency of the platform and a radius Rs of the platform and the outer diameter Ra of the vibrator in a mode in which n is an odd number.
Figure 15:
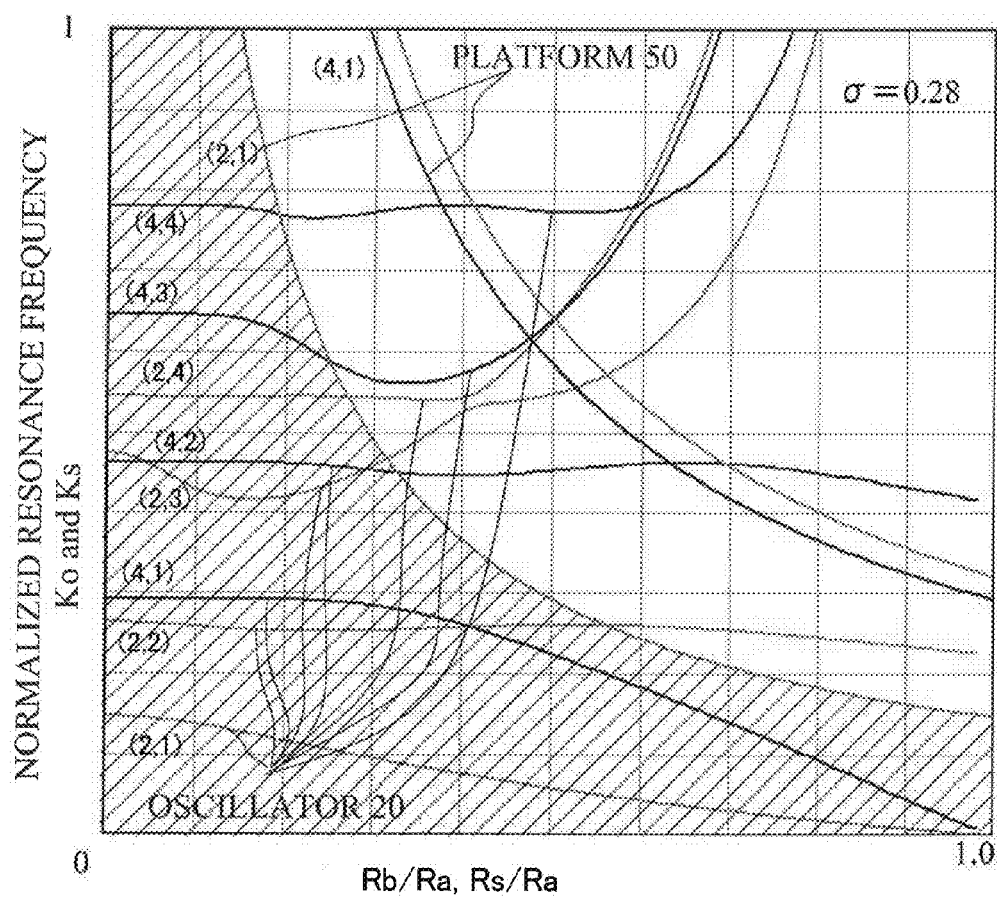
FIG. 15 is a diagram showing a relation between a resonance frequency of the vibrator and the inner diameter Rb and the outer diameter Ra of the vibrator and a relation between a resonance frequency of the platform and the radius Rs of the platform and the outer diameter Ra of the vibrator in a mode in which n is an even number.

A relation between normalized resonance frequencies Ko in the respective modes in the vibrator 20 and a ratio Rb/Ra of the inner diameter Rb and the outer diameter Ra of the vibrator 20 and a relation between normalized resonance frequencies Ks in the respective modes in the platform 50 and a ratio Rs/Ra of the radius Rs of the platform 50 and the outer diameter Ra of the vibrator 20 in this case are shown in FIGS. 14 and 15.

FIG. 14 is an example in the case in which n is an odd number. Single crystal Si is assumed as a material of the vibrator 20 and a Poisson's ratio is set to 0.28. Concerning the vibrator 20, resonance frequencies are calculated for n=1, 3 and m=1 to 4 in the Compound Mode. Concerning the platform 50, resonance frequencies are calculated for n=1, 3 and m=1 in a lowest order mode. Actual resonance frequencies can be calculated from formula (15).

[Formula 15]

$$K = \omega R_a \sqrt{\rho/E} \tag{15}$$

where, K is the normalized resonance frequency $K_o$ of the vibrator 20 or the normalized resonance frequency $K_s$ of the platform 50, Ra is an outer diameter of the vibrator 20, ρ is density, and E is a Young's modulus.

As it is seen from FIG. 14, resonance frequencies of the vibrator 20 and resonance frequencies of the platform 50 intersect except in the m=1 mode of the vibrator 20. In other words, when it is attempted to set the inner diameter Rb of the vibrator 20, in which the platform 50 is provided, larger than necessary and increase an area of the platform 50, a vibration frequency of the platform 50 falls to be lower than a vibration frequency of the vibrator 20. This means that, in this area, the platform 50 may resonantly vibrate according to a vibration mode. It is likely that the platform 50 is not in a state in which the entire surface thereof is not uniformly vibrating simply through the mechanical coupling. Therefore, to prevent the resonant vibration from mixing in the platform 50, it is necessary that a resonance frequency of the platform 50 is in an area higher than a resonance frequency of the vibrator 20. Such an area is an area below a frequency curve of a (1, 1) mode having a lowest frequency of a parallel vibration mode. This area is indicated by hatching in the figure.

It goes without saying that, even when this condition is not satisfied, there is considered to be a condition under which resonant vibration is not excited in the platform 50. However, fine condition classification is necessary. It is necessary to more deeply perform researches and grasp conditions.

When n is an even number, the relations are as shown in FIG. 15.

FIG. 15 is an example in the case in which n is an even number. Single crystal Si is assumed as a material of the vibrator 20 and a Poisson's ratio is set to 0.28. Concerning the vibrator 20, resonance frequencies are calculated for n=2, 4 and m=1 to 4 in the Compound Mode. Concerning the platform 50, resonance frequencies are calculated for n=2, 4 and m=1 in a lowest order mode and m=1 in the Tangential Mode. As in the case in which n is an odd number, if the platform 50 is formed such that a size thereof is in an area indicated by hatching, vibration due to a mode does not occur in the platform 50. The platform 50 performs uniform rotational vibration.

According to the sensor 10 described above, since the platform 50 is provided to be mechanically coupled to the vibrator, the mass of a substance adhering or sticking onto the platform 50 acts as if the substance concentratedly adheres or sticks to places where the platform 50 is connected to the vibrator 20. Therefore, it is possible to improve sensitivity of the sensor 10.

In this way, the sensor 10 can perform highly sensitive detection of a substance having mass and detection of the mass. The vibrator 20 can be manufactured by the MEMS technology by using a so-called Si single crystal as a structural material. Therefore, it is also possible to manufacture the sensor 10 by incorporating the sensor in a chip identical with that of an Si semiconductor is formed.

The inventors repeated further examinations on the basis of the knowledge obtained by performing the examinations described above and found that it was particularly preferable to drive the vibrator 20 in m=1 and n=3, i.e., the (3, 1) mode in terms of improvement of sensitivity. Moreover, the inventors found that it is preferable to set φ=Rb/Ra to 0.65 to 0.81 for the vibrator 20 and it is also preferable to set φ to 0.70 to 0.78, in particular, 0.73 to 0.74 in the (3, 1) mode.

This is explained by using a specific example.

Figure 16:
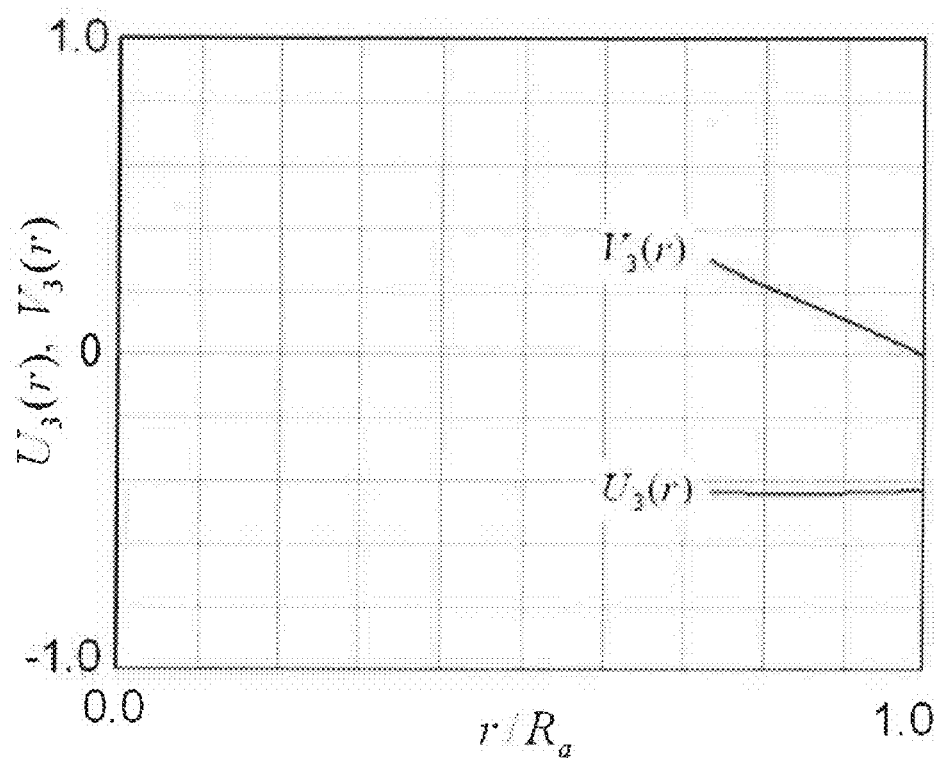
FIG. 16 is a diagram showing values of U(r) and V(r) in the position of the radius r of the disc-like vibrator in a (3, 1) mode.

In formula (10), when m=1 and n=3, a single crystal Si (the Poisson's ratio ρ=0.28, the Young's modulus E=130 GPa, the density σ=2300 kg/m³) is assumed as a material of the vibrator 20, and φ=Rb/Ra is set to 0.73, a calculation result is as shown in FIG. 16.

As shown in this FIG. 16, at r/Ra=1, i.e., in the outer diameter portion of the vibrator 20, $V_3$(Ra)=0. Therefore, displacement in the θ direction is always 0 in the outer diameter portion of the vibrator 20. $U_3$ (r, θ), which is a mode function in the r direction, is also a function of cos 3θ and $U_3$(r, θ) is 0 at θ=π/6±iπ (i=0, 1, 2, ... ). Therefore, displacement in the r direction at these angles is also 0. In other words, in the vibrator 20 with φ=0.73, there is no vibration in positions P1 to P6 in six places at angles θ=π/6, θ=3π/6, 5π/6, 7π/6, 9π/6, and 11π/6 in the outer diameter portion. In other words, if the vibrator 20 is held in these positions, vibration energy is not lost through the holding unit.

Figure 17:
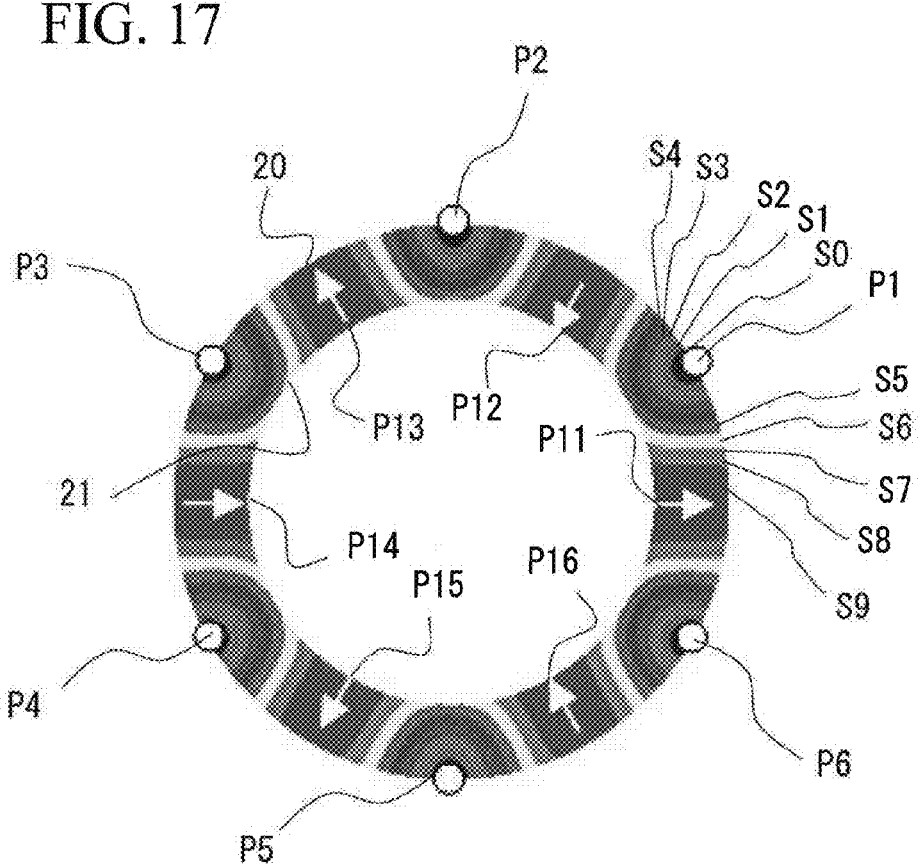
FIG. 17 is a diagram showing a distribution of amplitudes of the disc-like vibrator in the (3, 1) mode.

A mode figure in this example is shown in FIG. 17. In FIG. 17, magnitudes of vibration amplitudes on the vibrator 20 are shown by being sectioned into ten stages. A portion indicated by S0 is amplitude minimum (zero) and a portion indicated by S9 is amplitude maximum.

It is seen from this FIG. 17 that, in the (3, 1) mode, the vibrator 20 has large vibration amplitude in positions P11 to P16 of six places at angles θ=0, 2π/6, 4π/6, 6π/6, 8π/6, and 10π/6 in the inner diameter portion of the vibrator 20. A magnitude of this vibration is extremely large amplitude 0.97 times as large as maximum amplitude.

Since a vibration component in these positions is sin 3θ=0, the vibration component is not vibration of the θ component but vibration of the r component. In respective sets of the position P11 at θ=0 and the position P14 at θ=6π/6, the position P12 at θ=2π/6 and the position P15 at θ=8π/6, and the position P13 at θ=4π/6 and the position P16 at θ=10π/6, which are formed by two places point-symmetrical with respect to the center of the vibrator 20, respectively, directions of vibration in the positions are aligned in an identical direction. Therefore, if the platform 50 is provided to be coupled in these positions, the platform 50 does not affect a vibration mode.

Figure 18:
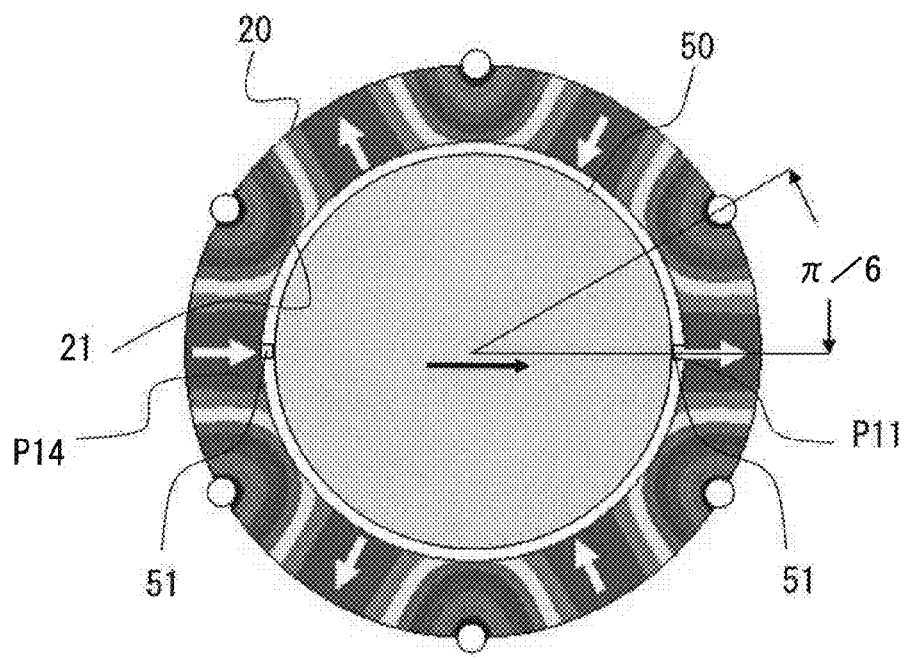
FIG. 18 is a diagram showing coupling positions in the case in which a platform is provided in the disc-like vibrator in the (3, 1) mode.

FIG. 18 is an example in which the platform 50 is provided in the opening 21 of the vibrator 20 in this (3, 1) mode. This is an example in which, in an inner peripheral portion of the vibrator 20 that vibrates in the (3, 1) mode, the platform 50 and the vibrator 20 are mechanically coupled by the bridges 51 in the positions P11 and P14 that are positions point-symmetrical with respect to the center of the vibrator 20 and where vibration amplitude is large. In this case, the entire surface of the platform 50 vibrates, due to the r component of the vibrator 20 in the (3, 1) mode, in the r direction corresponding to the positions of the vibrator 20 coupled by the bridges 51.

At this point, the platform 50 linearly displaces in a direction identical with a direction of the coupling positions by the bridges 51 in the vibrator 20. Therefore, it is possible to consider that this is equivalent to the fact that the mass of the vibrator 20 has approximately increased by the mass of the platform 50. A vibration frequency of the vibrator 20 falls because of the increase in the mass.

Table 1 shows a difference in a vibration frequency of the vibrator 20 according to presence or absence of the platform 50 in the case in which the outer diameter Ra of the vibrator 20 is 100 µm, the inner diameter Rb thereof is 73.4 µm, the outer diameter Rs of the platform is 70.7 µm, and the vibrator 20 and the platform 50 are formed of a single crystal silicon material.

TABLE 1

| Presence or absence of the platform | Oscillation frequency |
| --- | --- |
| Absent | 8.38 MHz |
| Present | 5.80 MHz |

In the above description, at $\phi \approx 0.73$, displacement in the $\theta$ direction is 0 in any direction in the outer diameter portion of the vibrator 20. Among the amplitude components of the mode function shown in formula (3) above, a Tangential component indicated by Vn(r) is formed by a Bessel function (a periodic function), and variables of the Bessel function are products of h, k, and r shown in formula (3) and are the same except the Poisson's ratio $\sigma$. Therefore, the Tangential component can also be regarded as a function of the Poisson's ratio $\sigma$.

Figure 7A:
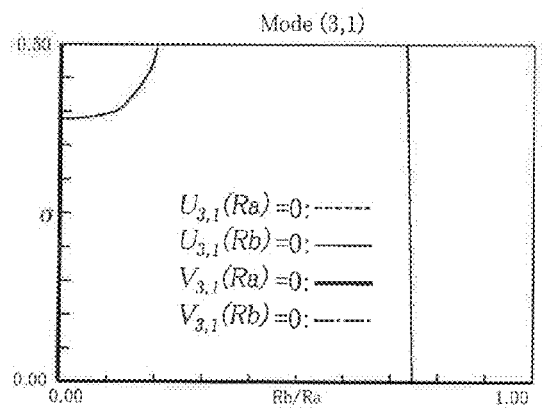
FIG. 7 is a diagram showing a relation between the ratio of the outer diameter and the inner diameter of the disc-like vibrator and the Poisson's ratio at the time when formula (12) holds in the n=3 mode.
Figure 7B:
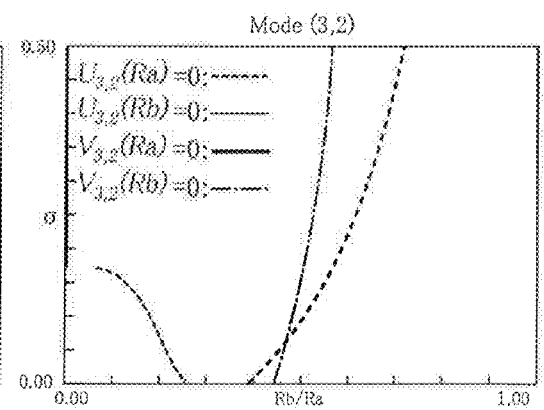
Figure 7C:
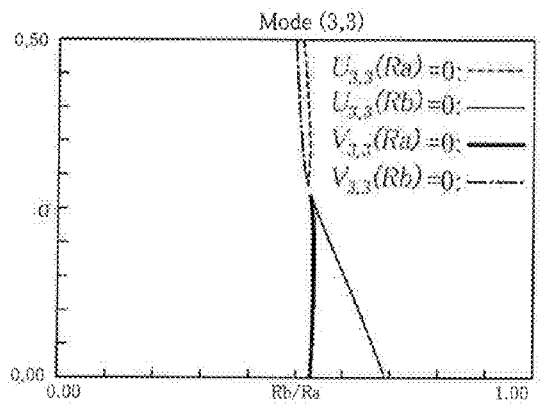
Figure 7D:
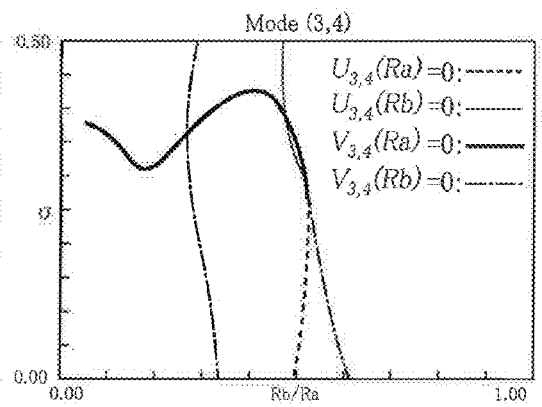

Consequently, when this relation is illustrated by plotting the Poisson's ratio $\sigma$, with which Vn(r)|r=Ra indicating vibration in the Tangential direction in the outer diameter portion of the vibrator 20 is 0, on the ordinate and plotting Rb/Ra on the abscissa, the relation is as shown in FIG. 7A.

Looking at this FIG. 7A, it is seen that, if Rb/Ra is selected to be near 0.73, dependency on a Poisson's ratio of a material of the vibrator 20 is extremely small. This means that a ratio of Rb/Ra hardly changes even if a Poisson's ratio of the material configuring the vibrator 20 fluctuates and means that designability for the Q value (the Quality Factor), which is considered to be a most important factor for the vibrator 20, is high. Therefore, it is preferable to set $\phi$ of the vibrator 20 to 0.70 to 0.78, in particular, 0.73 to 0.74.

In the above description, when a vibration mode of the vibrator 20 of a perforated disc type is the (3, 1) mode and the ratio $\phi$(Rb/Ra) of the inner diameter and the outer diameter is approximately 0.73, the six places where the vibrator 20 does not vibrate at all are generated on the outer periphery of the vibrator as shown in FIG. 17. If the vibrator 20 is held in these six places, vibration energy does not dissipate through the supporting members 22 and the vibrator 20 having high performance can be realized.

As shown in FIG. 18, if the platform 50 is mechanically connected by the bridges 51 in two places in the inner diameter portion that are symmetrical with respect to the center of the vibrator 20 and where an angle to the holding member 22 is 30 degrees ($\pi/6$), the platform 50 uniformly vibrates with the vibration of the vibrator 20.

However, it is expected that, by mechanically connecting the platform 50 to the vibrator 20 in such a form, the vibration of the vibrator 20 is affected and $\phi \approx 0.73$ and the like, which are conditions under which places where no vibration occurs are generated in six places, are affected in the outer diameter portion of the vibrator 20.

In other words, as shown in FIG. 18, when the platform 50 is attached to the vibrator 20 via the bridges 51, the platform 50 vibrates together with the vibrator 20. It is possible to consider that the mass of vibration of the vibrator 20 has approximately increased, i.e., the density of the vibrator has increased.

For example, when the outer diameter Ra of the vibrator 20 is set to 100 µm, the inner diameter Rb thereof is set to 73.4 µm, the outer diameter Rs of the platform 50 is set to 70.7 µm, and single crystal silicon (E=130 Gpa, $\rho$=2300 Kg/m³, $\sigma$=0.28) is used as a material of the vibrator 20, the mass of the vibrator 20 is calculated as indicated by formula (16):

[Formula 16]

$$M_R = \pi(R_a^2 - R_b^2)\rho t \quad (16)$$

The mass of the platform 50 is calculated as indicated by formula (17) and the overall mass of the vibrator 20 attached with the platform 50 is calculated as indicated by formula (18):

[Formula 17]

$$M_S = \pi R_s^2 \rho t \quad (17)$$

[Formula 18]

$$M_R = \pi(R_a^2 - R_b^2 + R_s^2)\rho t \quad (18)$$

When this state is grasped as a change in the density of the vibrator 20, it is possible to consider that an increase in the density of the vibrator 20 is calculated as indicated by formula (19):

[Formula 19]

$$\text{Rate of Change of } \rho: \frac{\pi(R_a^2 - R_b^2 + R_s^2)\rho t}{\pi(R_a^2 - R_b^2)\rho t} = 1 + \frac{R_s^2}{R_a^2 - R_b^2} \quad (19)$$

Even in such a state, when it is assumed that a characteristic value of the vibrator 20, i.e., Ko does not change, according to a relation of formula (20), a vibration frequency is originally 8.38 MHz from the density $\rho$=130 Gpa and Ko$\approx$0.70. When the platform 50 is attached, the density $\rho$ changes to $\rho$=130 Gpa*[1+Rs²/(Ra²-Rb²)] and the vibration frequency falls to 5.80 MHz.

[Formula 20]

$$K_0 = \omega_0 R_a \sqrt{\rho/E} \quad (20)$$

Figure 19:
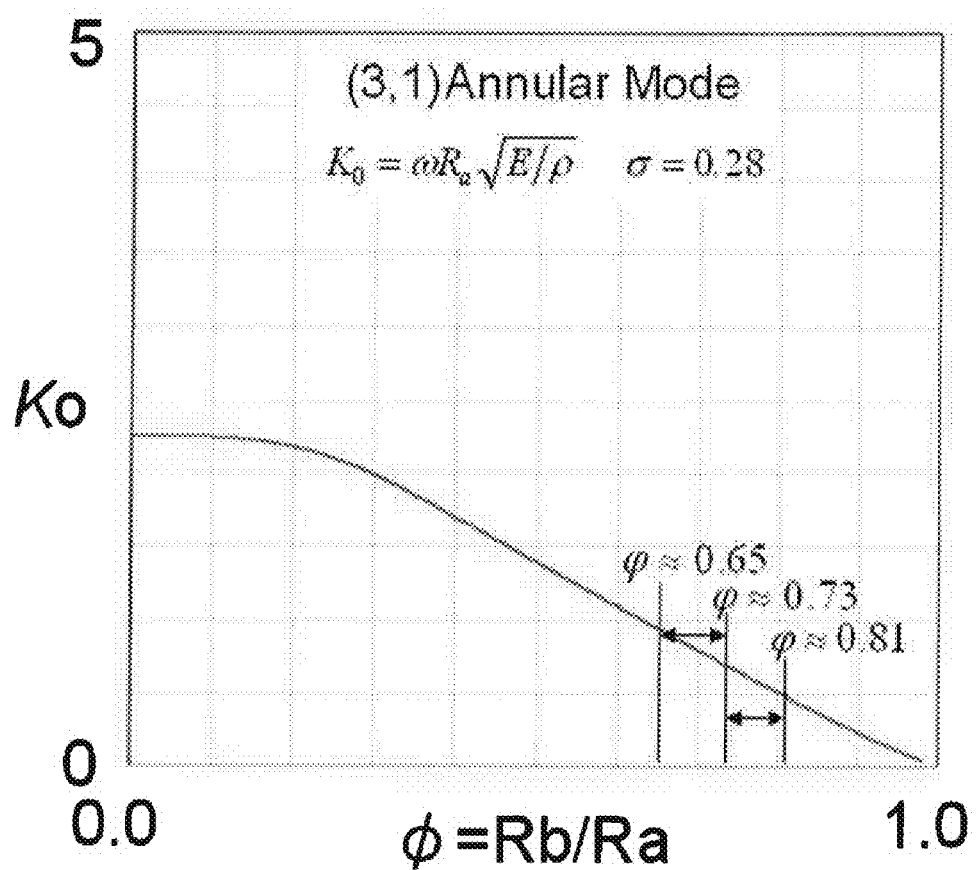
FIG. 19 is a diagram showing a relation between a vibration frequency parameter Ko of the disc-like vibrator and the inner diameter Rb and the outer diameter Ra of the vibrator in the (3, 1) mode.

FIG. 19 shows a relation between a vibration frequency parameter Ko and $\phi$=Rb/Ra of the vibrator 20 of a perforated disc type in the (3, 1) mode. In this relation, the vibration frequency parameter Ko and $\phi$=Rb/Ra is in a substantially linear relation at $\phi$>0.3. This relation can be approximately represented as indicated by formula (21):

[Formula 21]

$$K_0 = \omega R_a \sqrt{\rho/E} \approx 2.594(1-\phi) \rightarrow f_0 \approx \frac{1}{2\pi R_a}\sqrt{\frac{E}{\rho}} 2.594(1-\phi) \quad (21)$$

When the relation of formula (21) is applied to FIG. 19 and a change in a frequency is grasped as a change in Ko, it is seen that the change is equivalent to a change of $\phi$ from 0.73 to about 0.81. Even in such a case, when it is assumed that a shape of the vibration mode is kept as it is, the six places where the vibrator 20 does not vibrate at all in the outer diameter portion thereof continue to present as they are.

On the other hand, in FIG. 7A, looking at a state at $\phi \approx 0.81$, a state that satisfies $V_{3,1}$(Ra)=0 is not present. It is possible to consider this state as a state in which vibration energy escapes through the supporting members 22 provided in the outer diameter portion of the vibrator 20. It is seen by calculating formula (19) and formula (21) that, even when the platform 50 is provided, if φ is set small in advance, for example, set to about 0.65 and the platform 50 is provided such that a frequency at the time of φ=0.73 in a state without a platform is obtained, this state changes to a state at φ≈0.73.

It is possible to consider that, by estimating an vibration state of the vibrator 20 from fluctuation in a frequency in this way, a best value could change from 0.65 to about 0.81.

Figure 20:
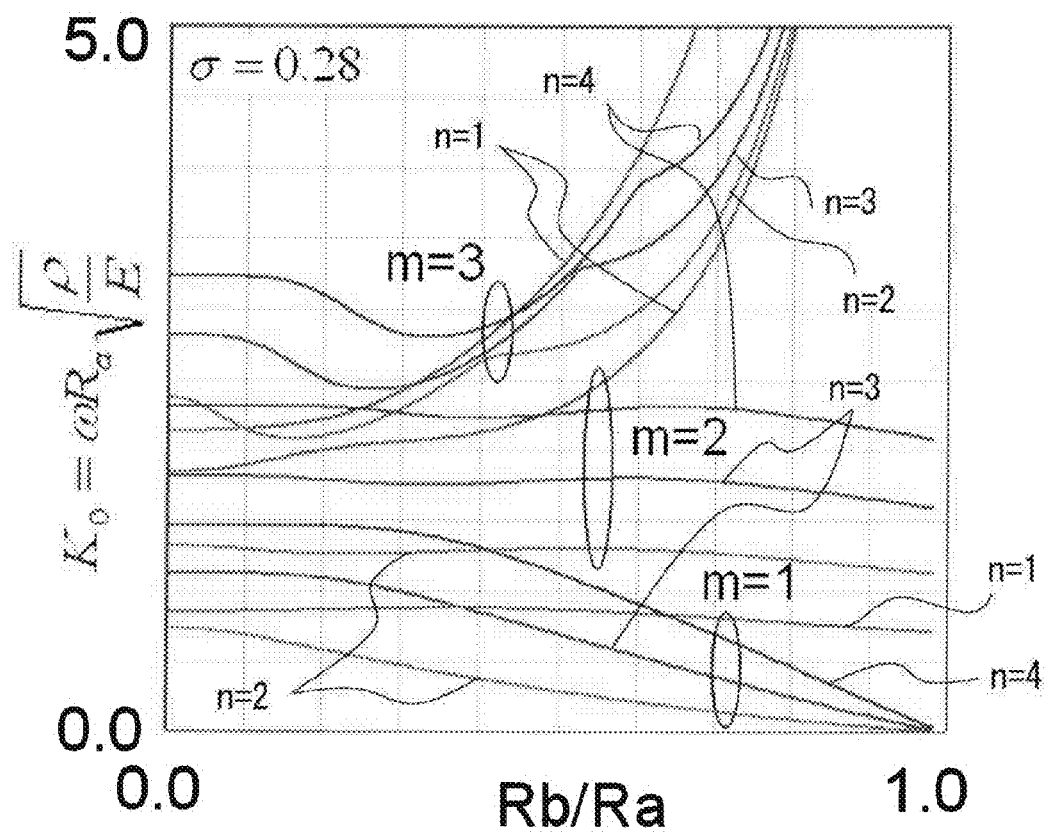
FIG. 20 is a diagram showing a relation between a resonance frequency and the inner diameter Rb and the outer diameter Ra of the vibrator in each of vibration modes.

Next, when a relation between the normalized resonance frequencies Ko in the respective modes in the vibrator 20 and the ratio Rb/Ra of the inner diameter Rb and the outer diameter Ra of the vibrator 20 at Rb/Ra≈0.73 is checked, the relation is as indicated by FIG. 20.

The (3, 1) mode currently under examination here is the case of n=3 and m=1. It is seen from FIG. 20 that a mode in which a resonance frequency lower than that in this (3, 1) mode is generated in only the (2, 1) mode. For example, when a semiconductor device such as a transistor and this vibrator 20 are combined to configure a transmitter, in general, the semiconductor device such as the transistor has a higher amplification degree as a frequency is lower and has a transmission ability concerning a frequency lower than a target vibration frequency. Therefore, a vibration frequency in the (2, 1) mode is likely to be a spurious vibration frequency of the transmitter. Therefore, it is necessary to prevent vibration in this (2, 1) mode from occurring.

Figure 21:
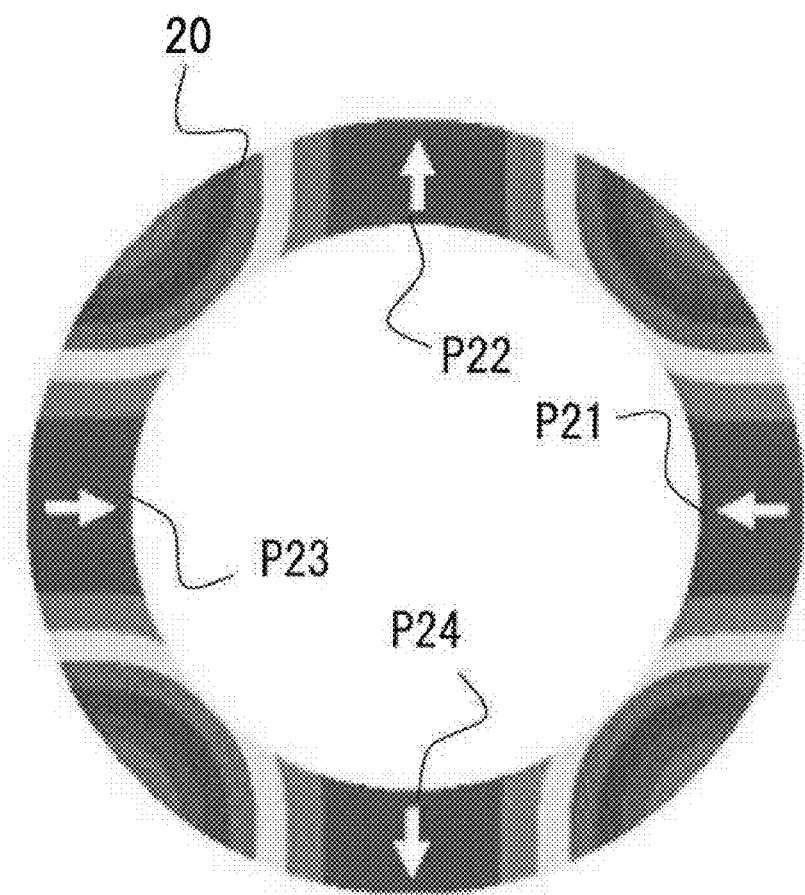
FIG. 21 is a diagram showing a distribution of amplitudes at the time when the vibrator in FIG. 17 vibrates in a (2, 1) mode.

FIG. 21 illustrates a vibration mode and an vibration direction in a maximum vibration area at Ra/Ra≈0.73 in the vibrator 20. In FIG. 21, it is seen that the vibrator 20 in the (2, 1) mode has large vibration amplitude in four positions P21 to P24 in places at angles θ=0, π/2, 2π/2, and 3π/2 in the inner diameter portion and the outer diameter portion thereof. The vibrator 20 is vibrating in directions opposite to each other in the two positions P21 and P23 that are symmetrical with respect to the center of the vibrator 20 and where maximum vibration occurs. On the other hand, as shown in FIG. 7A, in the (3, 1) mode, in the vibrator 20, directions of vibration in the positions P11 and P14 corresponding to the positions P21 and P23 are identical. Therefore, when the platform 50 is provided via the bridges 51 in these two areas, the platform 50 vibrates integrally with the vibrator 20 without hindering the vibration of the vibrator 20 in the (3, 1) mode. However, the vibration of the vibrator 20 in the (2, 1) mode inputted to the platform 50 via the bridges 51 changes to vibration that crushes or stretches the platform 50 in a radial direction in an in-plane direction of the platform 50. Therefore, the platform 50 displays an effect of controlling the vibration in the (2, 1) mode.

In the vibrator 20, a portion where vibration is large and a portion where vibration is small in the (2, 1) mode are always held by holding three places of the outer diameter portion of the vibrator 20 at intervals of 120°. This also hinders the vibration in the (2, 1) mode. Therefore, the platform 50 functions as a vibration control mechanism in the (2, 1) mode.

Figure 22:
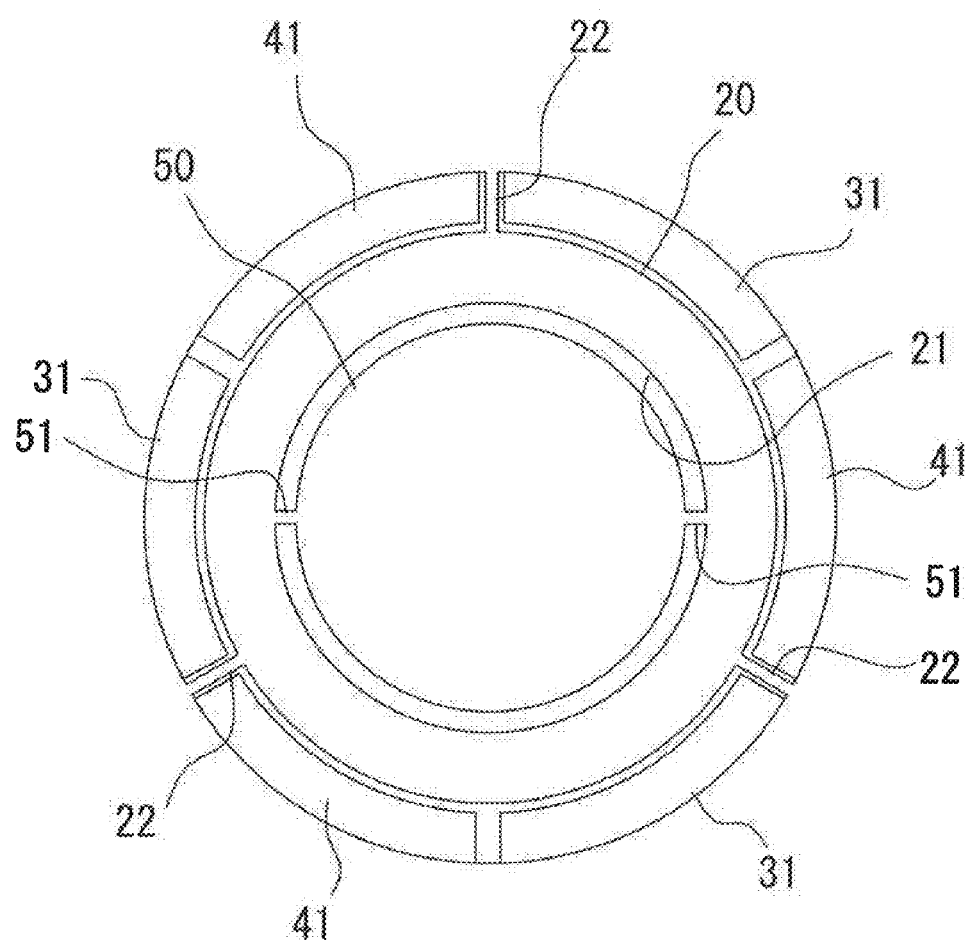
FIG. 22 is a diagram showing an example of the structure in which a platform is provided in the disc-like vibrator in the (3, 1) mode.

FIG. 22 is an example of the vibrator 20 including the platform 50 configured on the basis of the knowledge obtained on the basis of the examination described above.

This vibrator 20 is caused to vibrate in the (3, 1) mode and used. A ratio φ of an inner diameter and an outer diameter of the vibrator 20 is set to Rb/Ra=0.73. This vibrator 20 is held in three places at angles θ=3π/6, 7π/6, and 11π/6 in the outer diameter portion by the supporting members 22 at intervals of 120°.

The platform 50 is integrally joined to the opening 21 formed in the vibrator 20 via the bridges 51. The bridges 51 are provided, at intervals of 180°, in two places at θ=0 and 6π/6 that are positions point-symmetrical with respect to the center of the vibrator 20 and where vibration amplitude is large.

It is preferable that the vibrator 20, the platform 50, and the bridges 51 are located in an identical plane. These members can be formed of an identical material.

In an outer peripheral portion of the vibrator 20, electrodes 31 and 41 configuring the driving source 30 and the detection unit 40 are provided with a predetermined clearance apart from the outer diameter portion of the vibrator 20. These electrodes 31 and 41 are arranged pair by pair between the two supporting members 22 adjacent to each other.

According to the sensor 10 including the vibrator 20 having the structure described above, it is possible to perform highly sensitive detection of a substance having mass and detection of the mass as described above. Such a vibrator 20 can also be manufactured by the MEMS technology by using a so-called Si single crystal as a structural material. Therefore, it is also possible to manufacture the sensor 10 by incorporating the sensor in a chip identical with that of an Si semiconductor is formed.

In the vibrator 20 of a disc type described above that includes the platform 50 and vibrates in the (3, 1) mode to be used, the ratio φ of the outer diameter and the inner diameter is as large as 0.7 or more and an area of the platform 50 can be increased. Consequently, it is possible to set the sensitivity of the sensor 10 particularly high. If the ratio of the outer diameter and the inner diameter of the vibrator 20 is within the range described above, dependency on a material is low. Therefore, for example, even when a material more excellent than the single crystal Si appears in future, it is possible to apply a configuration same as the present invention. In addition, in such a configuration, since the vibration in the (2, 1) mode can be controlled, resonance is prevented. In this connection, it is also possible to realize improvement of sensitivity.

The example of the vibrator 20 in which the Si single crystal (the Poisson's ratio σ=0.28) is used as the material thereof is described above. However, it goes without saying that it is possible to realize a configuration that can obtain the same effect using other materials by performing the same examination.

In the example shown in FIG. 22, the vibrator 20 is supported at fixed points in the three places at the intervals of 120°. However, the vibrator 20 may be supported at all fixed points in the six places. If a supporting unit that supports the vibrator 20 can be a supporting unit mechanically having sufficiently high strength, the vibrator 20 may be supported in only one place. In the example shown in FIG. 22, three each of the electrodes 31 and 41 configuring the driving source 30 and the detection unit 40 are provided. However, it is also possible to reduce the number as appropriate. In general, when a coupling area of the electrodes 31 and 41 for driving and detection is reduced, a pass-through loss due to impedance mismatch caused by an increase in operation impedance increases. However, when a transmitter is manufactured, the increase in the pass-through loss can be compensated for by securing a sufficient loop gain.

Besides, it is possible to select the configurations referred to in the embodiment and change the configurations to other configurations as appropriate without departing from the spirit of the present invention.

The invention claimed is:

1. A detection sensor comprising:
   a disc-like vibrator;
   a platform that is mechanically coupled to the vibrator and to which a substance having mass adheres or sticks;

a driving unit that causes the vibrator to vibrate; and a detection unit that detects the substance by detecting a change in vibration in the vibrator, wherein an opening is formed in a center of the vibrator, and the platform is arranged on an inner side of the opening and coupled to an inner edge of the opening of the vibrator via bridges.

2. The detection sensor according to claim 1, wherein the platform is formed such that a resonance frequency thereof is higher than a resonance frequency of the vibrator.

3. A detection sensor comprising:

a disc-like vibrator;

a platform that is mechanically coupled to the vibrator and to which a substance having mass adheres or sticks;

a driving unit that causes the vibrator to vibrate; and a detection unit that detects the substance by detecting a change in vibration in the vibrator, wherein the platform is coupled to the vibrator in a position where the platform behaves integrally with the vibrator.

4. The detection sensor according to claim 3, wherein the platform is coupled to the vibrator in a region where vibration occurs only in one of a Radial direction and a Tangential direction of the vibrator in the vibrator.

5. The detection sensor according to claim 4, wherein the platform performs, integrally with the vibrator, linear vibration in the Radial direction of the vibrator or rotational vibration in the Tangential direction of the vibrator.

6. The detection sensor according to claim 3, wherein the platform is coupled to a region where amplitude is the largest or a portion near the region in the vibrator.

7. The detection sensor according to claim 1, wherein the platform is coupled to the vibrator in positions point-symmetrical or line-symmetrical with respect to the center of the vibrator.

8. The detection sensor according to claim 1, wherein the vibrator is formed in a ring shape, an outer diameter of which is represented as Ra and an inner diameter of which is represented as Rb because the opening is formed in the center, and the vibrator is formed with the outer diameter Ra and the inner diameter Rb with which displacement U(r) in a Radial direction and displacement V(r) in a Tangential direction, which are represented by formula (1), in a position r in a position coordinate (r, θ) at the time when the vibrator vibrates substantially satisfy U(r)=0 or V(r)=0 when r is Ra or Rb:

[Formula 1]

$$U(r) = \frac{\partial}{\partial r}J_n(hr) + A_6\frac{n}{r}J_n(kr) + A_7\frac{\partial}{\partial r}Y_n(hr) + A_8\frac{n}{r}Y_n(kr) \quad (1)$$

$$V(r) = \frac{n}{r}J_n(hr) + A_6\frac{\partial}{\partial r}J_n(kr) + A_7\frac{n}{r}Y_n(hr) + A_8\frac{\partial}{\partial r}Y_n(kr)$$

Where $$h = \omega\sqrt{\frac{\rho(1-\sigma^2)}{E}},$$

$$k = \omega\sqrt{\frac{\rho(2+2\sigma)}{E}},$$

$$k = h\sqrt{\frac{2}{1-\sigma}}$$

σ: Poisson's ratio of a vibrator material, E: Young's modulus of the vibrator material, ρ: the density of the vibrator material, ω: angular frequency, n: order of a vibration mode, A6, A7, A8: coefficients uniquely determined according to a peculiar vibration mode defined by an outer diameter and an inner diameter of a vibrator, the Young's modulus, the density, and the Poisson's ratio of the vibrator material, and boundary conditions (in this case, Free-Free conditions) of the vibrator.

9. The detection sensor according to claim 8, wherein, in the case in which U(r)=0 or V(r)=0 is substantially satisfied when r is Ra in the formula (1), the vibrator is supported in an outer diameter portion thereof.

10. A detection sensor comprising:

a disc-like vibrator;

a platform that is mechanically coupled to the vibrator and to which a substance having mass adheres or sticks;

a driving unit that causes the vibrator to vibrate; and a detection unit that detects the substance by detecting a change in vibration in the vibrator, wherein an opening is formed in a center of the vibrator, and the platform is coupled to an inner edge of the opening of the vibrator via bridges, and the driving unit drives the vibrator in a (3, 1) mode in which an order m of harmonic vibration is set to 1 and a modal number n of a vibration mode is set to 3.

11. The detection sensor according to claim 10, wherein, in the vibrator, when an outer diameter is represented as Ra and an inner diameter of the opening is represented as Rb, Rb/Ra is 0.65 to 0.81.

12. The detection sensor according to claim 10, wherein the vibrator is supported in plural positions where vibration in a Radial direction and a Tangential direction of the vibrator is substantially zero in an outer diameter portion thereof, and supporting positions of the vibrator are at intervals of an angle of 60° with respect to the center of the vibrator or intervals an integer times as large as 60°.

13. The detection sensor according to claim 12, wherein the vibrator is supported in three places at intervals of 120°.

14. The detection sensor according to claim 10, wherein the platform is coupled to the opening of the vibrator in two places where the platform behaves integrally with the vibrator and that are symmetrical with respect to the center of the vibrator.

15. The detection sensor according to claim 14, wherein the platform is coupled to the opening of the vibrator in a position in the vibrator where vibration in a (2, 1) mode in which an order m of harmonic vibration is 1 and a modal number n of a vibration mode is 2 is suppressed.

* * * * *